(12) United States Patent
Rossomando et al.

(10) Patent No.: US 10,328,125 B2
(45) Date of Patent: *Jun. 25, 2019

(54) TREATMENTS FOR NEUROLOGICAL DISORDERS

(75) Inventors: Anthony Rossomando, South Grafton, MA (US); Frank Porreca, Tuscon, AZ (US); Dinah Wen-Yee Sah, Boston, MA (US)

(73) Assignee: GLORIANA THERAPEUTICS, INC., Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/280,772

(22) PCT Filed: Feb. 27, 2007

(86) PCT No.: PCT/US2007/005365
§ 371 (c)(1),
(2), (4) Date: Feb. 27, 2009

(87) PCT Pub. No.: WO2007/100898
PCT Pub. Date: Sep. 7, 2007

(65) Prior Publication Data
US 2009/0221495 A1    Sep. 3, 2009

Related U.S. Application Data

(60) Provisional application No. 60/777,493, filed on Feb. 27, 2006, provisional application No. 60/863,852, filed on Nov. 1, 2006.

(51) Int. Cl.
*A61K 38/18*    (2006.01)

(52) U.S. Cl.
CPC .............................. *A61K 38/1883* (2013.01)

(58) Field of Classification Search
None
See application file for complete search history.

(56) References Cited

U.S. PATENT DOCUMENTS

| | | | |
|---|---|---|---|
| 4,352,883 A | 10/1982 | Lim | |
| 4,353,888 A | 10/1982 | Sefton | |
| 4,407,957 A | 10/1983 | Lim | |
| 4,883,666 A | 11/1989 | Sabel et al. | |
| 4,968,733 A | 11/1990 | Muller et al. | |
| 4,976,859 A | 12/1990 | Wechs | |
| 5,084,350 A | 1/1992 | Chang et al. | |
| 5,158,881 A | 10/1992 | Aebischer et al. | |
| 5,194,596 A | 3/1993 | Tischer et al. | |
| 5,284,761 A | 2/1994 | Aebischer et al. | |
| 5,350,836 A | 9/1994 | Kopchick et al. | |
| 5,414,135 A | 5/1995 | Snow et al. | |
| 5,445,934 A | 8/1995 | Fodor et al. | |
| 5,496,804 A | 3/1996 | Reed et al. | |
| 5,525,464 A | 6/1996 | Drmanac et al. | |
| 5,618,531 A | 4/1997 | Cherksey | |
| 5,641,749 A | 6/1997 | Yan et al. | |
| 5,650,494 A | 7/1997 | Cerletti et al. | |
| 5,654,007 A | 8/1997 | Johnson et al. | |
| 5,733,729 A | 3/1998 | Lipshutz et al. | |
| 5,754,524 A | 5/1998 | Wark | |
| 5,770,577 A | 6/1998 | Fandl et al. | |
| 5,775,320 A | 7/1998 | Patton et al. | |
| 5,780,014 A | 7/1998 | Eljamal et al. | |
| 5,780,019 A | 7/1998 | Klier et al. | |
| 5,785,049 A | 7/1998 | Smith et al. | |
| 5,795,716 A | 8/1998 | Chee et al. | |
| 5,798,113 A | 8/1998 | Dionne et al. | |
| 5,800,992 A | 9/1998 | Fodor et al. | |
| 5,814,607 A | 9/1998 | Patton | |
| 5,834,029 A | 10/1998 | Bellamkonda et al. | |
| 5,846,935 A | 12/1998 | Panayotatos | |
| 5,916,555 A | 6/1999 | Lee et al. | |
| 5,939,524 A | 8/1999 | Bowditch et al. | |
| 6,063,757 A | 5/2000 | Urso | |
| 6,083,725 A | 7/2000 | Selden et al. | |
| 6,084,076 A | 7/2000 | Ejima et al. | |
| 6,284,540 B1 | 9/2001 | Milbrandt et al. | |
| 6,299,895 B1 | 10/2001 | Hammang et al. | |
| 6,361,771 B1 | 3/2002 | Tao et al. | |
| 6,593,133 B1 | 7/2003 | Johansen et al. | |
| 6,677,135 B1 | 1/2004 | Sanicola-Nadel et al. | |
| 6,723,344 B2 | 4/2004 | Sakiyama-Elbert et al. | |
| 6,734,284 B1 | 5/2004 | Johansen et al. | |

(Continued)

FOREIGN PATENT DOCUMENTS

| | | |
|---|---|---|
| EP | 1 373 503 | 11/2007 |
| EP | 1 930 439 | 6/2008 |

(Continued)

OTHER PUBLICATIONS

Silvian L et al. Artemin crystal structure reveals insights into heparan sulfate binding. Biochemistry, Jun. 2006; 45(22):6801-12.*
Yan M et al. Two-amino acid molecular switch in an epithelial morphogen that regulates binding to two distinct receptors. Science, 2000; 290:523-527.*
Connell LA et al. Somatosensory impairment after stroke: frequency of different deficits and their recovery. Clin Rehabil. 2008; 22(8):758-767 (Abstract Only).*
Abrams et al., "Emerging strategies to promote improved functional outcome after peripheral nerve injury," Restor. Neurol. Neurosci., 23(5-6):367-82 (2005).
Aebischer et al, "Recombinant proteins for neurodegenerative diseases: the delivery issue," Trends in Neuroscience, Elsevier, Amsterdam, NL 24(9):533-540 (2001).
Aebischer et al., "Intrathecal delivery of CNTF using encapsulated genetically modified xenogeneic cells in amyotrophic lateral sclerosis patients," Nature Medicine, 2:696-699 (1996).
Airaksmen et al., GDNF family neurotrophic factor signaling: four masters, one servant, Mol. Cell Neurosci., 13:313-325 (1999).

(Continued)

*Primary Examiner* — Adam Weidner
(74) *Attorney, Agent, or Firm* — Lathrop Gage LLP; Ann-Louise Kerner

(57) ABSTRACT

Disclosed are methods of improving impaired proprioception, treating brachial plexus injuries, regenerating large and small nerve fibers, treating dorsal root nerve injuries, and improving sensory neural responses in a subject by administration of a neublastin polypeptide.

19 Claims, 14 Drawing Sheets

Specification includes a Sequence Listing.

(56) References Cited

U.S. PATENT DOCUMENTS

| | | |
|---|---|---|
| 7,067,473 B1 | 6/2006 | Masure |
| 7,115,257 B1 | 10/2006 | Tao et al. |
| 7,276,580 B2 | 10/2007 | Sah et al. |
| 7,358,228 B2 | 4/2008 | Sah et al. |
| 7,442,370 B2 | 10/2008 | Sah et al. |
| 7,598,059 B2 | 10/2009 | Pederson et al. |
| 7,601,518 B2 | 10/2009 | Wahlberg et al. |
| 7,655,463 B2 | 2/2010 | Sah et al. |
| 2002/0002269 A1 | 1/2002 | Milbrandt et al. |
| 2002/0055467 A1 | 5/2002 | Johansen et al. |
| 2002/0114780 A1 | 8/2002 | Bankiewicz et al. |
| 2003/0078373 A1 | 4/2003 | Fersht et al. |
| 2003/0100497 A1 | 5/2003 | Baker et al. |
| 2003/0166537 A1 | 9/2003 | Hanke |
| 2003/0186267 A1 | 10/2003 | Feder et al. |
| 2004/0028613 A1 | 2/2004 | Quay |
| 2004/0077543 A1 | 4/2004 | Sah et al. |
| 2004/0142418 A1 | 7/2004 | Sah et al. |
| 2004/0230043 A1 | 11/2004 | Johansen et al. |
| 2004/0242472 A1 | 12/2004 | Shelton et al. |
| 2004/0265972 A1 | 12/2004 | Weintraub et al. |
| 2005/0069520 A1 | 3/2005 | Shi et al. |
| 2005/0089960 A1 | 4/2005 | Wahlberg et al. |
| 2005/0118157 A1 | 6/2005 | McMahon et al. |
| 2005/0142098 A1 | 6/2005 | Sah et al. |
| 2005/0158824 A1 | 7/2005 | Pedersen et al. |
| 2005/0180957 A1 | 8/2005 | Scharp et al. |
| 2005/0181991 A1 | 8/2005 | Shelton et al. |
| 2005/0233359 A1 | 10/2005 | Masure et al. |
| 2006/0009625 A1 | 1/2006 | Bedows et al. |
| 2006/0014288 A1 | 1/2006 | Kim et al. |
| 2006/0122135 A1 | 6/2006 | Geerts et al. |
| 2007/0238650 A1 | 10/2007 | Sah et al. |
| 2007/0254842 A1 | 11/2007 | Bankiewicz |
| 2008/0039385 A1 | 2/2008 | Rossomando et al. |
| 2008/0227703 A1 | 9/2008 | Johansen et al. |
| 2008/0249287 A1 | 10/2008 | Rossomando et al. |
| 2008/0260702 A1 | 10/2008 | Jorgensen |
| 2008/0306212 A1 | 12/2008 | Sah et al. |
| 2009/0221495 A1 | 9/2009 | Rossomando et al. |
| 2009/0258831 A1 | 10/2009 | Sah |
| 2010/0056440 A1 | 3/2010 | Rossomando et al. |
| 2010/0234293 A1 | 9/2010 | Johansen et al. |
| 2010/0261654 A1 | 10/2010 | Rossomando et al. |
| 2010/0292142 A1 | 11/2010 | Sah et al. |

FOREIGN PATENT DOCUMENTS

| | | |
|---|---|---|
| JP | 11-310600 | 11/1999 |
| JP | 2002-534957 | 10/2002 |
| JP | 2003-310258 | 11/2003 |
| RU | 2225728 | 8/1999 |
| WO | WO 92/19195 | 11/1992 |
| WO | WO 93/06116 | 4/1993 |
| WO | WO 95/05452 | 2/1995 |
| WO | WO 97/08196 | 3/1997 |
| WO | WO 97/11964 | 4/1997 |
| WO | WO 97/19693 | 6/1997 |
| WO | WO 98/32869 | 7/1998 |
| WO | WO 99/03887 | 1/1999 |
| WO | WO 99/13090 | 3/1999 |
| WO | WO 99/42486 | 8/1999 |
| WO | WO 99/43813 | 9/1999 |
| WO | WO 99/49039 | 9/1999 |
| WO | WO 00/01815 | 1/2000 |
| WO | WO 00/04050 | 1/2000 |
| WO | WO 00/15665 | 3/2000 |
| WO | WO 00/17360 | 3/2000 |
| WO | WO 00/18799 | 4/2000 |
| WO | WO 00/34475 | 6/2000 |
| WO | WO 00/73348 | 12/2000 |
| WO | WO 01/47946 | 7/2001 |
| WO | WO 01/53486 | 7/2001 |
| WO | WO 01/66164 | 9/2001 |
| WO | WO 01/76639 | 10/2001 |
| WO | WO 01/87925 | 11/2001 |
| WO | WO 02/46430 | 6/2002 |
| WO | WO 02/051433 | 7/2002 |
| WO | WO 02/060929 | 8/2002 |
| WO | WO 02/072826 | 9/2002 |
| WO | WO 02/078730 | 10/2002 |
| WO | WO 03/44055 | 5/2003 |
| WO | WO 2004/002763 | 1/2004 |
| WO | WO 2004/069176 | 8/2004 |
| WO | WO 2004/094592 | 11/2004 |
| WO | WO 2004/108760 | 12/2004 |
| WO | WO 2005/039643 | 5/2005 |
| WO | WO 2006/023781 | 3/2006 |
| WO | WO 2006/023782 | 3/2006 |
| WO | WO 2007/042040 | 4/2007 |
| WO | WO 2007/100898 | 9/2007 |
| WO | WO 2007/103182 | 9/2007 |
| WO | WO 2008/137574 | 11/2008 |
| WO | WO 2009/020964 | 2/2009 |

OTHER PUBLICATIONS

Alfano et al., "The major determinant of the heparin binding of glial cell-line-derived neurotrophic factor is near the N-terminus and is dispensable for receptor binding," Biochem. J., 404(1):131-40 (2007).

Algvere et al., "Transplantation of RPE in age-related macular degeneration: observations in disciform lesions and dry RPE atrophy," Graefe's Arch. Clin. Exp. Ophthalmol., 235:149-158 (1997).

Anderson, "Human gene therapy," Nature, 392:25-30 (1998).

Andres et al., "Multiple effects of artemin on sympathetic neurone generation, survival and growth," Development 128:3685-3695 (2001).

Anonymous, "Anti-human Artemin Antibody," R&D Systems Product Data Sheets (Dec. 27, 2006), [online] XP002505114. Retrieved from the Internet: www.rndsystems.com/pdf/AF2589.pdf [retrieved on Nov. 21, 2008].

Anonymous, "Monoclonal Anti-human Artemin Antibody," R&D Systems Product Data Sheets (Mar. 23, 2006), [online] XP002505115. Retrieved from the Internet: http://www.rndsystems.com/pdf/MAB2589.pdf [retrieved on Nov. 21, 2008].

Atschul et al., "Gapped BLAST and PSI-BLAST: a new generation of protein database search programs," Nucl. Acids Res., 25:3389-3402 (1997).

Baloh et al. "Artemin, a novel member of the GDNF ligand family, supports peripheral and central neurons and signals through the GFRalpha3-RET receptor complex," Neuron, 21(6):1291-1302 (1998).

Baloh et al., "Functional mapping of receptor specificity domains of glial cell line-derived neurothropic factor (GDNF) family ligands and production of GFR alpha 1 RET-specific agonists," J. of Biological Chemistry, 275(5):3412-3420 (2000).

Baudet et al., "Positive and negative interactions of GDNF, NTN and ART in developing sensory neuron subpopulations, and their collaboration with neurotrophins," Development, 127:4335-4344 (2000).

Bauskin et al., "The propeptide of macrophage inhibitory cytokine (MIC-1), a TGF-β superfamily member, acts as a quality control determinant for correctly folded MIC-1," The EMBO Journal, 19(10):2212-2220 (2000).

Bendtsen et al., "Improved prediction of signal peptides—SignalP 3.0," J. Mol. Biol., 340(4):783-795 (2004).

Bennett et al., "Artemin has potent neurotrophic actions on injured C-fibres," J. Peripher. Nerv. Syst., 11(4):330-45 (2006).

Bonde et al., "GDNF and neublastin protect against NMDA-induced excitotoxicity in hippocampal slice cultures," Neuroreport., 11:4069-4073 (2000).

Bootcov et al., "MIC-1, a novel macrophage inhibitory cytokine, is a divergent member of the Tgf-β superfamily," Pro. Natl. Acad. Sci. U.S.A., 94:11514-11519 (1997).

Bork, "Go hunting in sequence databases but watch out of the traps," Trends in Genetics, 12:425-427 (1996).

Bork, "Powers and Pitfalls in Sequence analysis: the 70% Hurdle," Genome Research, 10:398-400 (2000).

(56) References Cited

OTHER PUBLICATIONS

Borodovsky et al., "Detection of new genes in a bacterial genome using Markov models for three gene classes," Nucl. Acids Res., 23:3554-3562 (1995).
Boucher et al "Artemin prevents injury-induced changes in small sensory neurons," Abstracts of the Society for Neuroscience, Society for Neuroscience, Washington D.C. 26(1/2):63305 (2000).
Brenner, "Errors in genome annotation," Trends in Genetics, 15:132-133 (1999).
Burgess et al., "Possible dissociation of the heparin-binding and mitogenic activities of heparin-binding (acidic fibroblast) growth factor-1 from its receptor-binding activities by site-directed mutagenesis of a single lysine residue," J. of Cell Biology, 111:2129-2138 (1990).
Callister et al., Soc. For Neuroscience Abstracts 27(1):36.11 (2001).
Campbell et al., "Mechanisms of Neuropathic Pain," Neuron, 52:77-92 (2006).
Carmillo et al., "Glial Cell Line-Derived Neurotrophic Factor (GDNF) Receptor α-1(GFRα1) Is Highly Selective for GDNF versus Artemin," Biochemistry, 44:2545-2554 (2005).
Ceyhan et al., "The neurotrophic factor artemin promotes pancreatic cancer invasion," Ann. Surg., 244:274-81 (2006).
Ceyhan et al., "The neurotrophic factor artemin influences the extent of neural damage and growth in chronic pancreatitis," Gut., 56(4):534-44 (2007).
Damon et al., "Vascular-derived artemin: a determinant of vascular sympathetic innervation?," Am. J. Physiol. Heart Circ. Physiol., 293:H266-H273 (2007).
Daopin et al., "Crystal structure of TGF-β2 refined at 1.8 A resolution," Proteins, 17:176-192 (1993).
Delgado et al., "The uses and properties of PEG-Linked proteins," Critical Reviews in Therapeutic Drug Carrier Systems, 9(3/4):249-304 (1992).
Doerks et al., "Protein annotation: detective work for function prediction," Trends in Genetics, 14:248-250 (1998).
During et al., "Towards gene therapy for the central nervous system," Mol. Med., 11:485-493 (1998).
Eigenbrot et al., "X-ray structure of glial cell-derived neurotrophic factor at 1 9 A resolution and implications for receptor binding," Nat. Struct. Biol., 4:435-438 (1997).
Enomoto et al., "RET signaling is essential for migration, axonal growth and axon guidance of developing sympathetic neurons," Development, 128:3963-3974 (2001).
Enzmann et al., "Immunological problems of transplantation into the subretinal space," Acta Anat., 162:178-183 (1998).
Fairlie et al., "The propeptide of the transforming growth factor-β superfamily member, macrophage inhibitory cytokine-1 (MIC-1), is a multifunctional domain that can facilitate protein folding and secretion," J. of Biol. Chem., 276(20):16911-16918 (2001).
Finsen et al., "Somatostatin and neuropeptide Y in organotypic slice cultures of the rat hippocampus: an immunocytochemical and in situ hybridization study," Neurosci., 47:105-113 (1992).
Fjord-Larsen, et al. "Efficient in vivo protection of nigral dopaminergic neurons by lentiviral gene transfer of a modified Neurturin construct," Experimental Neurology, 195:49-60 (2005).
Flanders et al., "TGFβ," Laboratory of Cell Regulation and Carcinogenesis, National Cancer Institute, 719-746 (undated).
Francis et al., "Pegylation of Cytokines and other therapeutic proteins and peptides: the importance of biological optimization of coupling techniques," Int'l. Journal of Hematology, Elsevier Science Publishers, NL., 68(1):1-18 (1998).
Friedmann, "Principles for human gene therapy studies," Science, 287:2163-2164 (2000).
Gardell et al., "Multiple actions of systemic artemin in experimental neuropathy," Nat Med., 9(11):1383-89 (2003).
GenBank Accession No. AA844072, 2 pages (1998).
GenBank Accession No. AC005037, Waterston, 54 pages (1998).
GenBank Accession No. AC005038, Sulston et al., 96 pages (2001).
GenBank Accession No. AC005051, Waterston, 38 pages (1998).
GenBank Accession No. AF040962, Milbrandt et al., 2 pages (1998).
Genbank Accession No. AF120274, Rosenblad et al., 3 pages (1999).
Gilchuk, "Assessment of renaturation methods for industrial producing recombinant proteins in biologically active form from *E. coli* inclusion bodies," Biopolymers and Cell, 20(3):182-192 (2004).
Griffin et al., "Assessment of cutaneous innervation by skin biopsies," Current Opinion in Neurology, 14:655-659 (2001).
Guerra et al., "PEGylation prevents the N-terminal degradation of megakaryocyte growth and development factor," Pharm. Res., 15(12):1822-1827 (1998).
Gustafsson, "New insights in oestrogen receptor (ER) research—the ERbeta," Eur. J. Cancer, 36 Suppl. 4:S16 (2000).
Hall et al., "Eukaryotic and Prokaryotic Signal Peptides Direct Secretion of a Bacterial Endoglucanase by Mammalian Cells," Journal of Biological Chemistry, 265(32):19996-19999 (1990).
Hallböök et al., "Expression of Neurotrophins and Trk Receptors in the Avian Retina," J. Compar. Neurol., 364:664-676 (1996).
Hamilton et al., "Heparin coinfusion during convection-enhanced delivery (CED) increases the distribution of the glial-derived neurotrophic factor (GDNF) ligand family in rat striatum and enhances the pharmacological activity of neurturin," Experimental Neurology, 168:155-161 (2001).
Hoane et al. "Mammalian-Cell-Produced Neurturin (NTN) Is More Potent Than Purified *Escherichia coli*-Produced NTN," Exp. Neurol., 162:189-193 (2000).
Israel et al., "Acetylcholine Release and the Cholinergic Genomic Locus," Molecular Neurobio., 16(1):1-20 (1998).
Johansen et al., "Biosynthesis of peptide precursors and protease inhibitors using new consititutive and inducible eukaryotic expression vectors," FEBS Lett., 267:289-294 (1990).
Kim et al., "An experimental model for peripheral neuropathy produced by segmental spinal nerve ligation in the rat," Pain, 50:355-363 (1992).
Kirsch et al. "Expression of ciliary neurotrophic factor receptor mRNA and protein in the early postnatal and adult rat nervous system," Neurosci. Lett., 180:163-166 (1994).
Kotzbauer et al., "Neurturin, a relative of glial-cell-line-derived neurotrophic factor," Nature, 384:467-70 (1996).
Kron et al., "Coronary revascularization rather than cardiac transplantation for chronic ischemic cardiomyopathy," Ann. Surg., 210:348-352 (1989).
Lapchak et al., "Pharmacological characterization of glial cell line-derived neurotrophic factor (GDNF): implications for GDNF as a therapeutic molecule for treating neurodegenerative diseases," Cell Tissue Res., 286:179-189 (1996).
Lapchak, "Therapeutic potential for glial cell line-derived neurotropic factor (GDNF) based upon pharmacological activities in the CNS," Rev. Neurosci., 7:165-176 (1977).
Lavail et al., "Protection of mouse photoreceptors by survival factors in retinal degenerations," Invest. Ophthalmol. Vis. Sci., 39(3):592-602 (1998).
Lee et al., "Proliferin Secreted by Cultured Cells Binds to Mannose 6-Phosphate", J. Biol. Chem., 263(7):3521-3527 (1988).
Lee et al., "Prolonged circulating lives of single-chain Fv proteins conjugated with polyethylene glycol: a comparison of conjugation chemistries and compounds," Bioconjug. Chem., 10:973-981 (1999).
Li et al., "beta-Endorphin omission analogs: dissociation of immunoreactivity from other biological activities," PNAS, 77(6):3211-14 (1990).
Li et al., "Expression, purification, and characterization of recombinant human neurturin secreted from the yeast *Pichia pastoris*," Protein Expression and Purification, 30(1):11-17 (2003).
Lin et al., "GDNF: A glial cell line-derived neurotrophic factor for midbrain dopaminergic neurons," Science, 260:1130-1132 (1993).
Little et al., "Transplantation of human fetal retinal pigment epithelium rescues photoreceptor cells from degeneration in the royal college of surgeons rat retina," Invest. Ophthalmol. Vis. Sci., 37(1):204-211 (1996).
Lorenz et al., "Heteromultimeric CLC chloride channels with novel properties," Proc. Natl. Acad. Sci USA, 93:13362-13366 (1996).

(56) References Cited

OTHER PUBLICATIONS

Maeda et al., "Efficient Production of Active TNF α by albumin Signal Peptide," Biochemistry and Molecular Biology International, Academic Press, London, GB, 42(4):825-832 (1997).
Massague et al., "The TGF-βfamily and its composite receptor," Trends Cell Biol., 4:172-178 (1994).
Mason, "The RET receptor tyrosine kinase: activation, signalling and significance in neural development and disease," Pharm. Acta. Helv., 74:261-4 (2000).
Masure et al., "Enovin, a novel member of the GDNF family of neurotrophic growth factors with growth promoting and neuroprotective effects on neuronal cells," a poster presentation from Janssen Research Foundation, "Gordon Conference" held on Jun. 6-11, 1999.
Masure, et al., "Enovin, a member of the glial cell-line-derived neurotrophic factor (GDNF) family with growth promoting activity on neuronal cells," Eur J. Biochem., 266:892-902 (1999).
Masure et al., "Mammalian GFRalpha-4, a divergent member of the GFRalpha family of coreceptors for glial cell line-derived neurotrophic factor family ligands, is a receptor for the neurotrophic factor persephin," J. Biol. Chem., 275:39427-34 (2000).
Matsushita et al., "Cloning and structural organization of the gene encoding the mouse glial cell line-derived neurotrophic factor, GDNF," Gene, 203:149-157 (1997).
Mcdonald et al., "A structural superfamily of growth factors containing a cystine knot motif.," Cell, 73:421-424 (1993).
Merlo et al. "The Mouse int-2 Gene Exhibits Basic Fribroblast Growth Facctor Activity in a Basic Fibroblast Growth Factor-responsive Cell Line," Cell Growth & Differentiation, 1:463-472 (1990).
Milbrandt et al., "Persephin, a novel neurotrophic factor related to GDNF and Neurturin," Neuron, 20:245-253 (1998).
Moore et al., "Renal and neuronal abnormalities in mice lacking GDNF," Nature, 382:76-79 (1996).
Moustakas et al., "Smad regulation in TGF-β signal transduction," J. of Cell Science, 114:4359-4369 (2001).
Ngo et al., "The Protein Folding Problem and Tertiary Structure Prediction," Birkhäuser, 492-495 (1994).
Nielsen et al., "Identification of prokaryotic and eukaryotic signal peptides and prediction of their cleavage sites," Protein Engineering, 10(1):1-6 (1997).
Nielsen et al., "Prediction of signal peptides and signal anchors by a hidden Markov model," Proceedings of the 6th International Conference on Intelligent systems for Molecular Biology, 122-130 (1998).
Nishino et al., "GFR alpha3, a component of the artemin receptor, is required for migration and survival of the superior cervical ganglion," Neuron, 23(4):725-736 (1999).
Norton et al., "Bacterial beta-Galactosidase as a Marker of Rous Sarcoma Virus Gene Expression and Replication," Mol. Cell. Biol., 5:281-290 (1985).
Orozco et al., "Nociceptive Neurons Express GFRα3," Society for Neuroscience, Abstracts 26 (1-2): Abstract No. 412.7 (2000).
Orozco et al., "GFRalpha3 is expressed predominantly in nociceptive sensory neurons," Eur. J. Neurosci., 13(11):2177-82 (2001).
Palmiter, "Heterologous introns can enhance expression of transgenes in mice," PNAS, 88:478-482 (1991).
Park et al., "Coordinated interaction of the vascular and nervous systems: from molecule- to cell-based approaches," Biochem. Biophys. Res. Commun., 311:247-253 (311) (2003).
Pawson et al., "Assembly of cell regulatory systems through protein interaction domains," Science, 300:445-452 (2003).
Rakowicz et al., "Glial Cell Line-Derived Neurotrophic Factor Promotes the Survival of Early Postnatal Spinal Motor Neurons in the Lateral and Medial Motor Columns in Slice Culture," The Journal of Neuroscience, 22(10):3953-3962 (2002).
Rattenholl et al., "Pro-sequence assisted folding and disulfide bond formation of human nerve growth factor," J. Mol. Biol., 305:523-533 (2001).
Rattenholl et al., "The pro-sequence facilitates folding of human nerve growth factor from *Escherichia coli* inclusion bodies," Eur. J. Biochem., 268:3296-3303 (2001).
Reddy, "Controlled-release peylation, liposomal formulations: new mechanisms in the delivery of injectable drugs," Annals of Pharmacotherapy, 34(7/8):915-923 (2000).
Reinshagen et al., "Commercial recombinant human β-Nerve Growth factor and adult rat dorsal root ganglia contain an identical molecular species of nerve growth factor prohormone," J. of Neurochemistry, 74:2127-2133 (2000).
Riganti et al., "Nitroarginine methyl ester and canavanine lower intracellular reduced glutathione," Free Radic. Biol. Med., 35(10):1210-6 (2003).
Robertson et al., "The GDNF-RET signaling in partnership," Trends Genet., 13:1-3 (1997).
Rosenberg et al., "Gene therapist, heal thyself," Science, 287:1751 (2000).
Rosenberg et al., "Vectors for selective expression of cloned DNAs by T7 RNA polymerase," Gene, 56:125-135 (1987).
Rosenblad et al., "In vivo protection of nigral dopamine neurons by lentiviral gene transfer of the novel GDNF-family member neublastin/artemin," Molecular and Cellular Neuroscience, 15(2):199-214 (2000).
Rosenblad et al., "In vivo protection of nigral dopamine neurons by lentiviral gene transfer of the novel GDNF-family member neublastin/artemin," Mol. Cell Neurosci., 18(3):332-333 (2001).
Saarma et al., "Other neurotrophic factors: glial cell line-derived neurotrophic factor (GDNF)," Microsc. Res. Tech., 45(4-5):292-302 (1999).
Saarma, "GDNF: A stranger in the TGF-beta superfamily?" European Journal of Biochemistry, 267(24):6968-6971 (2000).
Sadick et al., "Analysis of heregulin-induced ErbB2 phosphorylation with a high-throughput Kinase receptor activation enzyme-linked immunosorbant assay," Anal. Biochem., 235(2):207-14 (1996).
Sah et al., "Prevention and Reversal of Experimental Neuropathic Pain by Systemic Neublastin," Society for Neuroscience Abstracts, 27(1):361 (2001).
Sah et al., "New approaches for the treatment of pain: the GDNF family of neurotrophic growth factors," Curr. Top Med. Chem., 5(6):577-83 (2005).
Sanicola et al., "Glial cell line-derived neurotrophic factor-dependent RET activation can be mediated by two different cell-surface accessory proteins," Proc Natl Acad Sci, USA, 94:6238-6243 (1997).
Sauer et al., "Progressive degeneration of nigrostriatal dopamine neurons following intrastraiatal terminal lesions with 6-hydroxydopamine: a combined retrograde tracing and immunocytochemical study in the rat," Neuroscience, 59:401-415 (1994).
Schmidt et al. "In vivo kinetics as a sensitive method for testing physiologically intact human recombinant apolipoprotein A-1: comparison of three different expression systems," Clinica Chimica Acta, 268(1-2):41-60 (1997).
Skolnick et al. "From genes to protein structure and function: novel applications of computational approaches in the genomic era," Trends in Biotech., 18(1):34-39 (2000).
Sloot et al., "Detection of salicylate and its hydroxylated adducts 2.3- and 2.5-dihydroxybenzoic acids as possible indices for in vivo hydroxyl radical formation in combination with catechol- and indoleamines and their metabolites in cerebrospinal fluid and brain tissue," J. Neurosci. Meth., 60:141-149 (1995).
Smith et al. "The challenges of genome sequence annotation" or "The devil is in the details," Nature Biotechnology, 15:1222-1223 (1997).
Stoppini et al., "A simple method for organotypic cultures of nervous tissue," J. Neurosci. Methods, 37:173-182 (1991).
Thompson et al., "The ClustalX windows interface: flexible strategies for multiple sequence alignment aided by quality analysis tools," Nucl. Acids Res., 25:4876-4882 (1997).
Tseng et al., "Neurturin protects dopaminergic neurons following medial forebrain bundle axotomy," Mol. Neurosci, 9:1817-1822 (1998).
Unsicker, "GDNF: a cytokine at the interface of TGF-betas and neurotrophins," Cell Tissue Res., 286:175-178 (1996).

(56) References Cited

OTHER PUBLICATIONS

Vallejo et al., "Optimized procedure for renaturation of recombinant human bone morphogenetic protein-2 at high protein concentration," Biotechnol. Bioeng., 85(6):601-609 (2004).
Varmus, "Gene therapy: Not ready for prime time," Nature Medicine, 2(1):7-8 (1996).
Verma et al., "Gene therapy—promises, problems and prospects," Nature, 389:239-242 (1997).
Verma, "Gene therapy: beyond 2000," Mol. Ther., 6:493 (2000).
Veronese et al., "Introduction and Overview of Peptide and Protein Pegylation," Advanced Drug Delivery Reviews, 54(4):453-456 (2002).
Von Schwedler et al., "Vif is crucial for human immunodeficiency virus type 1 proviral DNA synthesis in infected cells," J. Virol., 67:4945-4955 (1993).
Vukicevic et al., "Induction of nephrogenic mesenchyme by osteogenic protein 1 (bone morphogenetic protein 7)," PNAS USA, 93:9021-9026 (1996).
Wang et al., "Single-chain Fv with manifold N-glycans as bifunctional scaffolds for immunomolecules," Protein Eng., 11(12):1277-83 (1998).
Wang et al., "Animal and cellular models of chronic pain ," Adv. Drug Delivery Rev., 55:949-965 (2003).
Wang et al., "Inhibitory effect of endostatin expressed by human liver carcinoma SMMC7721 on endothelial cell proliferation in vitro," World Journal of Gastroenterology, 8(2):253-257 (2002).
Watabe et al., "Spontaneously immortalized adult mouse Schwann cells secrete autocrine and paracrine growth-promoting activities," J. Neurosci. Res., 41:279-90 (1995).
Wefstaedt et al., "Neurotrophic factors of the GDNF family and their receptors are detectable in spiral ganglion cells of normal hearing as well as of deafened rats," Laryngorhinootologie, 85(11):802-8 (2006) (English abstract only, see p. 807).
Wells, "Additivity of Mutational Effects in Proteins," Biochemistry, 29:8509-8517 (1990).
West et al., "Estimation of the Number of Somatostatin Neurons in the Striatum: An In Situ Hybridization Study Using the Optical Fractionator Method," J. Comp. Neurol., 370:11-22 (1996).
White et al., "Chemokines: integrators of pain and inflammation," Nat Rev. Drug discovery 4:834-844 (2005).
Zufferey et al., "Multiply attenuated lentiviral vector achieves efficient gene delivery in vivo," Nat. Biotechnol., 15:871-875 (1997).
Airaksinen et al., "The GDNF family: signalling, biological functions and therapeutic value," Nature Reviews, Neuroscience 3:383-394 (May 2002).
Bennett et al., "A distinct subgroup of small DRG cells express GDNF receptor components and GDNF is protective for these neurons after nerve injury," J. Neurosci. 18(8):3059-3072 (Apr. 15, 1998).
Bennett, G., "An animal model of neuropathic pain: A review," Muscle & Nerve 16:1040-1048 (1993).
Frankel et al., "High-Level Expression and Purifcation of the Recombinant Diphtheria Fusion Toxin DTGM for PHASE I Clinical Trials," Expr Purif. 16(1):190-201, (Jun. 1999).
Freynhagen et al., "The evaluation of neuropathic components in low back pain," Current Pain & Headache Reports 13:185-190 (2009).
Machelska et al., "Breaking the pain barrier," Nature Medicine 9(11):1353-1354 (2003).

Mogyoros et al., "Strength-duration properties of sensory and motor axons in amyotrophic lateral sclerosis," Brain 121:851-859 (1998).
Park et al., "Tarnscriptional regulation of artemin is related to neurite outgrowth and actin polymerization in mature DRG neurons," Neuroscience Letters 404:61-66 (2006).
Pons et al., "Massive cortical reorganization after sensory deafferentation in adult macaques," Scient. 252(5014):1857-1860 (1991).
Ramachandran et al., "Perceptual correlates of massive cortical reorganization," Science 258(5085):1159-1160 (1992).
Ramachandran, "Behavioral and MEG correlates of neural plasticity in the adult human brain," Proceedings of the National Academy of Sciences 90:10413-10420 (1993).
Ramer et al., "Functional regeneration of sensory axons into the adult spinal cord," Nature 403:312-316 (Jan. 2000).
Rico et al., "Characterization of the immunostimulatory properties of Leishmania infantum HSP70 by fusion to the *Escherichia coli* maltose-binding protein in normal and nu/nu BALB/c mice," Infect Immun. 66:1347-352 (Jan. 1998).
Rossomando et al., "In vitro and in vivo characterization of neublastin, a nociceptive neuronal trophic factor," Abstracts of the Annual Meeting of the Society for Neuroscience, Society for Neuroscience, Washington, DC, U.S., 27(1):361 (2001) (XP001121851, ISSN: 0190-5295).
Sah et al., "Neurotrophic factors as novel therapeutics for neuropathic pain," Nature Reviews 2:460-472 (2003).
Snider et al., "Tackling pain at the source: new ideas about nociceptors," Neuron 20:629-632 (Apr. 1998).
Trupp et al., "Peripheral expression and biological ctivities of GDNF, a new neurotrophic factor for avian and mammalian peripheral neurons," The Journal of Cell Biology 130(1):137-148 (Jul. 1995).
Vickers, "A vaccine against Alzheimer's disease: developments to date." Drugs Aging 19(7):487-94 (2002).
Wang et al., "Persistent Restoration of sensory function by immediate or delayed systemic artemin after dorsal root injury," Nature Neurosci. 11(4):488-496 (2008).
Paveliev, M. et al., "GDNF family ligands activate multiple events during axonal growth in mature sensory neurons," *Molecular and Cellular Neuroscience*; (2004) 25(3):453-459.
Accession No. AF109402 (1998).
Fargrell, B. et al., "Disbursed microvascular reactivity and shunting—a major cause for diabetic complications," Vascular Medicine (1999); 4:125-127.
Honma et al., "Artemin is a vascular-derived neurotrophic factor for developing sympathetic neurons," Neuron 35(2):267-282 (2002).
L-arginine entry, (2009), Drugs.com drug information online, no author listed, 15 pages as printed.
Mills, C.D. et al., "Strain and model differences in behavioral outcomes after spinal cord injury in rat," J. Neurotrauma 18(8):743-56, 2001.
Purves, D. et al.; "The Cover, Dorsal view of the human brain," Neuroscience, Sinauer Associates, Inc., 2nd Ed., pp. 75, 367, 400, 403, 554, 555, and 678, 2001.
Stokes, B.T. et al., "Experimental modeling of human spinal cord injury: a model that crosses the species barrier and mimics the spectrum of human cytopathology," Spinal Cord 49:101-109, 2002.
Talac, R. et al., "Animal models of spinal cord injury for evaluation of tissue engineering treatment strategies," Biomaterials 25:1505-1510, 2004.
Ulbrecht, J.S., et al., "Foot Problems in Diabetes: An Overview," Clinical Infectious Diseases (2004), 39:S73-82.

* cited by examiner

|                | | 10 | 20 | 30 | 40 | 50 |
|---|---|---|---|---|---|---|
| Human Neubla... | 1 | MELGLGGLST | LSHCPWPRRQ | PALWPTLAAL | ALLSSVAEAS | LGSAPRSPAP |
| Mouse Neubla... | 1 | MELGLAEPTA | LSHCLRPRWQ | SAWWPTLAVL | ALLSCVTEAS | LDPMSRSPAA |
| Rat Neublastin | 1 | MELGLGEPTA | LSHCLRPRWQ | PALWPTLAAL | ALLSSVTEAS | LDPMSRSPAS |
| Human Neubla... | 51 | REGPPPVLAS | PAGHLPGGRT | ARWCSGRARR | PPPQPSRPAP | PPPAP----P |
| Mouse Neubla... | 51 | RDGPSPVLAP | PTDHLPGGHT | AHLCSERTLR | PPPQSPQPAP | PPPGPALQSP |
| Rat Neublastin | 51 | RDVPSPVLAP | PTDYLPGGHT | AHLCSERALR | PPPQSPQPAP | PPPGPALQSP |
| Human Neubla... | 97 | SALPRGCRAA | RAGGPCSRAR | AAGARGCRLR | SQLVPVRALG | LGHRSDELVR |
| Mouse Neubla... | 101 | PAALRGARAA | RAGTRSSRAR | TTDARGCRLR | SQLVPVSALG | LGHSSDELIR |
| Rat Neublastin | 101 | PAALRGARAA | RAGTRSSRAR | ATDARGCRLR | SQLVPVSALG | LGHSSDELIR |
| Human Neubla... | 147 | FRFCSGSCRR | ARSPHDLSLA | SLLGAGALRP | PPGSRPVSQP | CCRPTRYEAV |
| Mouse Neubla... | 151 | FRFCSGSCRR | ARSQHDLSLA | SLLGAGALRS | PPGSRPISQP | CCRPTRYEAV |
| Rat Neublastin | 151 | FRFCSGSCRR | ARSPHDLSLA | SLLGAGALRS | PPGSRPISQP | CCRPTRYEAV |
| Human Neubla... | 197 | SFMDVNSTWR | TVDRLSATAC | GCLG | | |
| Mouse Neubla... | 201 | SFMDVNSTWR | TVDHLSATAC | GCLG | | |
| Rat Neublastin | 201 | SFMDVNSTWR | TVDHLSATAC | GCLG | | |

FIG. 1

6 Months after DRC

US 10,328,125 B2

TREATMENTS FOR NEUROLOGICAL DISORDERS

CROSS REFERENCE TO RELATED APPLICATIONS

This application is a national phase filing under 35 U.S.C. § 371 of International application No. PCT/US2007/005365, filed Feb. 27, 2007, which claims priority from provisional application No. 60/777,493 filed Feb. 27, 2006 and provisional application No. 60/863,852 filed Nov. 1, 2006 The entire content of the prior applications are incorporated herein by reference in their entirety.

TECHNICAL FIELD

The invention relates to protein chemistry, molecular biology, and neurobiology.

BACKGROUND

Neublastin, also known as artemin and enovin, is a 24 kDa homodimeric, secreted protein that promotes the outgrowth and survival of neurons of the peripheral and central nervous system (Baudet et al., 2000, *Development*, 127:4335; Masure et al., 1999, *Eur. J. Biochem.*, 266:892; Rosenblad et al., 2000, *Mol. Cell. Neurosci.*, 15(2):199). Neublastin mRNA is expressed predominantly in embryonic kidney and lung, and in adults, is expressed highest in pituitary gland, trachea, and placenta (Baudet et al., 2000, *Development*, 127:4335).

Neublastin is a member of the glial cell line-derived neurotrophic factor (GDNF) ligand family. GDNF ligands activate both Ras and phosphatidylinositol-3-kinase signal transduction pathways by engaging the membrane-bound c-RET receptor tyrosine kinase. This c-RET-mediated signaling requires an additional co-receptor, a glycosylphosphatidyl inositol (GPI)-anchored GDNF family receptor alpha (GFRα) protein, which confers ligand specificity to c-RET. Four GFRα co-receptor proteins have been identified (GFRα1-4). Neublastin shows highest affinity for GFRα3 in vitro, however in studies using human fibroblasts, neublastin can stimulate c-RET-dependent signaling through either GFRα3 or GFRα1 (Baudet et al., 2000, Development, 127:4335; Masure et al., 1999, *Eur. J. Biochem.* 266:892; Rosenblad et al., 2000, Mol. Cell. Neurosci. 15(2):199).

Neublastin and the other GDNF family members are members of the transforming growth factor beta (TGF beta) superfamily and thus, are characterized by the presence of seven conserved cysteine residues with similar spacing which form the structure of a cysteine knot (Saarma, 1999, *Microsc. Res. Tech.*, 45:292). Each monomer contains two disulfide bonds that form a closed loop structure encircling the third disulfide to form a tight knot structure. The seventh cysteine contained within each monomer forms an intermolecular disulfide bond, covalently linking the monomers to form the final dimer product (Rattenholl et al 2000, *J. Mol. Biol.*, 305:523).

SUMMARY

Injury of the dorsal roots results in significant and often irreversible loss of sensory functions due to apparent limited regenerative capacity of sensory axons as well as inhibitory barriers that prevent axonal entry into the spinal cord. The present invention is based, at least in part, on the surprising discovery that systemic administration of neublastin restores sensorimotor functions in animals that have undergone dorsal root crush. Together with this functional recovery, systemic administration of neublastin was found to promote reentry of multiple classes of primary afferent fibers though the dorsal root entry zone (DREZ) into the spinal cord and to brainstem nuclei, resulting in reestablished synaptic function. In addition to promoting recovery from dorsal root crush injury, systemic administration of neublastin was also found to promote peripheral nerve regeneration and recovery of mechanical and thermal hypersensitivity in animals that have undergone nerve crush distal to the dorsal root ganglia.

In one aspect, the invention features a method of improving impaired proprioception by administering, to a subject that exhibits impaired proprioception, an amount of a polypeptide effective to improve proprioception in the subject, wherein the polypeptide contains an amino acid sequence that is at least 80% identical to amino acids 15-113 of SEQ ID NO:1, wherein the polypeptide, when dimerized, binds to a complex containing GFRα3 and RET. Also disclosed is the use of the polypeptide for the preparation of a pharmaceutical composition for improving proprioception in subject that exhibits impaired proprioception.

As used herein, "proprioception" refers to the ability to sense, independent of vision, the location, orientation, and movement of the body and its parts.

In another aspect, the invention features a method of regenerating nerve fibers (e.g., dorsal root nerve fibers or nerve fibers distal to the dorsal root ganglia) by administering, to a subject that has suffered damage to or loss of nerve fibers, an amount of a polypeptide effective to regenerate nerve fibers, wherein the polypeptide contains an amino acid sequence that is at least 80% identical to amino acids 15-113 of SEQ ID NO:1, and wherein the polypeptide, when dimerized, binds to a complex containing GFRα3 and RET. Also disclosed is the use of the polypeptide for the preparation of a pharmaceutical composition for regenerating nerve fibers in a subject that has suffered damage to or loss of nerve fibers.

As used herein, "regenerating nerve fibers" refers to regrowth of lost or damaged nerve fibers. The nerve fibers can be large or small nerve fibers. For example, the nerve fibers can be nerve fibers of the skin (wherein administration of the polypeptide to the subject results in skin reinnervation). The damage to or loss of nerve fibers can be the result of, e.g., a nerve crush injury or a nerve cut injury.

In another aspect, the invention features a method of improving an impaired sensory neural response by administering, to a subject that exhibits an impaired sensory neural response, an amount of a polypeptide effective to improve the impaired response, wherein the polypeptide contains an amino acid sequence that is at least 80% identical to amino acids 15-113 of SEQ ID NO:1, and wherein the polypeptide, when dimerized, binds to a complex containing GFRα3 and RET. Also disclosed is the use of the polypeptide for the preparation of a pharmaceutical composition for improving a sensory neural response in subject that exhibits an impaired sensory neural response.

The impaired sensory neural response can be characterized by, e.g., a loss of sensitivity to noxious mechanical or thermal stimuli. The impaired sensory neural response can be a result of damage to or loss of dorsal root nerve fibers or nerve fibers distal to the dorsal root ganglia.

In another aspect, the invention features a method of treating a brachial plexus injury by administering, to a subject that has suffered a brachial plexus injury, an effective amount of a polypeptide that contains an amino acid sequence that is at least 80% identical to amino acids 15-113 of SEQ ID NO:1, wherein the polypeptide, when dimerized, binds to a complex containing GFRα3 and RET. Also disclosed is the use of the polypeptide for the preparation of a pharmaceutical composition for treating a subject with a brachial plexus injury.

In another aspect, the invention features a method of treating a dorsal root nerve injury by administering, to a subject that has suffered loss of synaptic function as a result of a dorsal root nerve injury, an amount of a polypeptide effective to promote reentry of nerve fibers through the dorsal root entry zone into the spinal cord, wherein the polypeptide comprises an amino acid sequence that is at least 80% identical to amino acids 15-113 of SEQ ID NO:1, and wherein the polypeptide, when dimerized, binds to a complex containing GFRα3 and RET. Also disclosed is the use of the polypeptide for the preparation of a pharmaceutical composition for treating a subject that has suffered a dorsal root nerve injury.

In some embodiments of the methods described herein, the polypeptide is administered to the subject within, e.g., 1, 2, 3, 4, 5, 6, 7, 8, 9, 10, 11, 12, 13, 14, 21, 28, 35, 42, 49 or 56 days following the impairment of proprioception, the damage to or loss of nerve fibers, the impairment of a sensory neural response, the brachial plexus injury, or the dorsal root nerve injury. The subject can be administered a single dose or multiple doses (e.g., 2, 3, 4, 5, 6, 7, or more doses) of the polypeptide. The polypeptide can optionally be administered to the subject intermittently (e.g., one dose per day, one dose every 2 or 3 days, or one dose per week) during a period of, e.g., 1, 2, 3, 4, or more weeks following the impairment of proprioception, the damage to or loss of nerve fibers, the impairment of a sensory neural response, the brachial plexus injury, or the dorsal root nerve injury. An "effective amount" of a polypeptide may comprise administering the polypeptide to the subject via multiple doses (e.g. two or more doses) over an extended period of time (e.g., days or weeks).

The polypeptide can optionally be administered to the subject for a limited period of time and/or in a limited number of doses following the impairment of proprioception, the damage to or loss of nerve fibers, the impairment of a sensory neural response, the brachial plexus injury, or the dorsal root nerve injury. For example, in some embodiments administration of the polypeptide to the subject can be terminated (i.e., no further administrations provided) within, e.g., one year, six months, one month, or two weeks following the impairment of proprioception, the damage to or loss of nerve fibers, the impairment of a sensory neural response, the brachial plexus injury, or the dorsal root nerve injury. In some embodiments, treatment of the subject entails administration of 50 or fewer total doses of the polypeptide (e.g., 40 or fewer doses, 30 or fewer doses, 20 or fewer doses, 15 or fewer doses, 10 or fewer doses, 9 or fewer doses, 8 or fewer doses, 7 or fewer doses, 6 or fewer doses, 5 or fewer doses, 4 or fewer doses, 3 or fewer doses, or 2 or fewer doses).

In some embodiments of the methods described herein, the polypeptide is administered to the subject via systemic administration (e.g., via subcutaneous or intravenous administration).

In some embodiments of the methods described herein, the polypeptide is administered locally to damaged neural tissue.

The subject treated according to the methods described herein can be a human or another mammal such as a mouse, rat, cow, pig, dog, cat, or monkey.

In another aspect, the invention features a method of regenerating nerve fibers by contacting neural tissue (e.g., dorsal root ganglia or nerve fibers distal to the dorsal root ganglia) that has suffered damage to or loss of nerve fibers with an amount of a polypeptide effective to regenerate nerve fibers, wherein the polypeptide contains an amino acid sequence that is at least 80% identical to amino acids 15-113 of SEQ ID NO:1, and wherein the polypeptide, when dimerized, binds to a complex containing GFRα3 and RET. The nerve fibers can be large or small nerve fibers. In some embodiments, the nerve fibers are nerve fibers of the skin In some embodiments, the damage to or loss of nerve fibers is the result of a nerve crush injury. In some embodiments, the damage to or loss of nerve fibers is the result of a nerve cut injury.

The neural tissue can be contacted with the polypeptide, e.g., within, e.g., 1, 2, 3, 4, 5, 6, 7, 8, 9, 10, 11, 12, 13, 14, 21, 28, 35, 42, 49 or 56 days following the damage to or loss of nerve fibers. The neural tissue can be contacted with a single dose or multiple doses (e.g., 2, 3, 4, 5, 6, 7, or more doses) of the polypeptide. The neural tissue can be contacted with the polypeptide intermittently (e.g., one dose per day, one dose every 2 or 3 days, or one dose per week) during a period of, e.g., 1, 2, 3, 4, or more weeks following the damage to or loss of nerve fibers.

In some embodiments of the methods described herein, the polypeptide contains an amino acid sequence is at least 90%, 95%, or 98% identical to amino acids 15-113 of SEQ ID NO:1.

In some embodiments of the methods described herein, the polypeptide contains an amino acid sequence is at least 90%, 95%, or 98% identical to SEQ ID NO: 1.

In some embodiments of the methods described herein, the polypeptide contains amino acids 15-113 of SEQ ID NO:1, amino acids 15-113 of SEQ ID NO:2, amino acids 15-113 of SEQ ID NO:3, amino acids 15-113 of SEQ ID NO:4, amino acids 15-113 of SEQ ID NO:5, amino acids 15-113 of SEQ ID NO:8, or amino acids 15-113 of SEQ ID NO:9.

In some embodiments of the methods described herein, the polypeptide contains amino acids 10-113 of SEQ ID NO:1.

In some embodiments of the methods described herein, the polypeptide contains the amino acid sequence of SEQ ID NO:1, the amino acid sequence of SEQ ID NO:2, the amino acid sequence of SEQ ID NO:3, the amino acid sequence of SEQ ID NO:4, the amino acid sequence of SEQ ID NO:5, the amino acid sequence of SEQ ID NO:8, or the amino acid sequence of SEQ ID NO:9.

An advantage of certain treatment methods described herein is the production of persistent axonal regeneration and restoration of sensory function following a limited number of systemic injections of neublastin, thereby obviating the requirement for a long-term treatment regime (of possibly indefinite duration) and/or for spinal infusions (and its associated risks).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is an alignment of wild type human (SEQ ID NO:10), mouse (SEQ ID NO:11), and rat (SEQ ID NO:12) pre pro neublastin polypeptides. The left and right vertical lines indicate, respectively, the start of the mature 113 amino and 104 amino acid forms. The RRXR heparin binding motif is boxed.

FIG. 4 (bottom) is a scatter plot of the maximum synaptic response to stimulation of the medial or radial nerve recorded in experimental animals. Each symbol represents the results from one animal, either after DRC or for unlesioned (intact) roots on the contralateral side of the same animal. The average maximum response for each group is shown with an open circle and vertical line (mean±1 S.E.). The groups tested at ~1 month included postoperative times of 0.7 to 1.4 months. All 9 animals treated with artemin showed substantial regeneration after DRC, with an average amplitude ¼ to ⅓ that of normal responses. None of the 8 vehicle-treated rats showed any appreciable regeneration after DRC.

DETAILED DESCRIPTION

Figure 2:
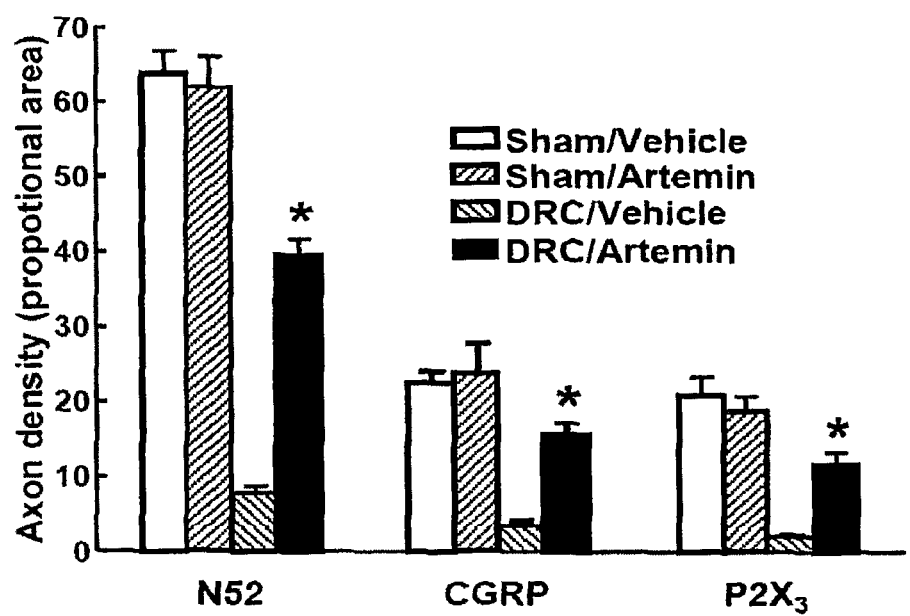
FIG. 2 is a graph depicting the effect of systemic neublastin (artemin) administration on axonal density in the dorsal root entry zone following dorsal root crush (DRC). Asterisks indicate significant differences from vehicle-treated rats with DRC.

The present invention provides methods of improving impaired proprioception, treating brachial plexus injuries, regenerating large and small nerve fibers, treating dorsal root nerve injuries, and improving sensory neural responses in a subject by administration of a neublastin polypeptide. As disclosed in the accompanying Examples, systemic administration of neublastin was found to restore sensory function in animals that have undergone dorsal root crush, promote reentry of nerve fibers though the DREZ into the spinal cord of injured animals, and promote peripheral nerve regeneration and recovery of mechanical and thermal hypersensitivity in animals that have undergone nerve crush distal to the dorsal root ganglia.

Neublastin Polypeptides

Mature wild type human neublastin is 113 amino acids in length and has the following amino acid sequence: AGGPGSRARAAGARGCRLRSQLVPVRALGLGHR SDELVRFRFCSGSCRRARSPHDLSLASLLGAGALRPP-PGSRPVSQPCCRPTRYEAV SFMDVNSTWRTVDRL-SATACGCLG (SEQ ID NO:1). Polypeptides having the amino acid sequence of SEQ ID NO:1 or biologically active variants of thereof can be used in the methods described herein. A variant neublastin polypeptide can contain one or more additions, substitutions, and/or deletions, as detailed in the following sections. Wild-type neublastin polypeptides and biologically active variants thereof are collectively referred to herein as "neublastin polypeptides."

A variant neublastin polypeptide can vary in length from the corresponding wild-type polypeptide. Although the mature human neublastin polypeptide (SEQ ID NO:1) consists of the carboxy terminal 113 amino acids of pre pro neublastin (SEQ ID NO:10), not all of the 113 amino acids are required to achieve useful neublastin biological activity. Amino terminal truncation is permissible. Thus, a variant neublastin polypeptide can contain, for example, the carboxy terminal 99, 100, 101, 102, 103, 104, 105, 106, 107, 108, 109, 110, 111, 112, or 113 amino acids of SEQ ID NO:1 (i.e., its length can be 99, 100, 101, 102, 103, 104, 105, 106, 107, 108, 109, 110, 111, 112, or 113 amino acids).

A variant neublastin polypeptide can also vary in sequence from the corresponding wild-type polypeptide. In particular, certain amino acid substitutions can be introduced into the neublastin sequence without appreciable loss of a neublastin biological activity. In exemplary embodiments, a variant neublastin polypeptide (i) contains one or more amino acid substitutions, and (ii) is at least 70%, 80%, 85%, 90%, 95%, 98% or 99% identical to SEQ ID NO:1 (or 70%, 80%, 85%, 90%, 95%, 98% or 99% identical to amino acids 15-113 of SEQ ID NO:1). A variant neublastin polypeptide differing in sequence from SEQ ID NO:1 (or differing in sequence from amino acids 15-113 of SEQ ID NO:1) may include one or more amino acid substitutions (conservative or non-conservative), one or more deletions, and/or one or more insertions.

FIG. 1 is an alignment of the wild type human, mouse, and rat pre pro neublastin polypeptides. The vertical lines in FIG. 1 indicate the start of the mature 113 amino acid form (left vertical line) and 104 amino acid form (right vertical line) of neublastin. The RRXR heparin binding motif is boxed. This alignment of naturally occurring, bioactive forms of neublastin indicates specific exemplary residues (i.e., those that are not conserved among the human, mouse, and rat forms) that can be substituted without eliminating bioactivity.

Percent identity between amino acid sequences can be determined using the BLAST 2.0 program. Sequence comparison can be performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et alt, 1997, *Nucleic Acids Research* 25:3389-3402.

A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

A biologically active variant neublastin polypeptide, when dimerized, binds to a ternary complex containing GFRα3 and RET. Any method for detecting binding to this complex can be used to evaluate the biological activity a variant neublastin polypeptide. Exemplary assays for detecting the ternary complex-binding ability of a variant neublastin polypeptide are described in WO00/01815 (the content of which is incorporated herein by reference).

A variant neublastin polypeptide can also be assessed to evaluate its ability to trigger the neublastin signaling cascade. For example, the Kinase Receptor Activation (KIRA) assay can be used to assess the ability of a variant neublastin polypeptide to induce RET autophosphorylation (See also, Sadick et al., 1996, *Anal. Biochem.*, 235(2):207).

Substitutions at one or more of the following amino acid residues are expected to result in a variant neublastin polypeptide having reduced or absent heparin binding ability as compared to wild type neublastin: Arg 48, Arg 49, Arg 51, Ser 46, Ser 73, Gly 72, Arg 39, Gln 21, Ser 20, Arg 68, Arg 33, His 32, Val 94, Arg 7, Arg 9, or Arg 14. Reference to a neublastin amino acid reside by position number refers to the numbering of residues relative to SEQ ID NO:1. A neublastin amino acid residue designated for substitution (e.g., an arginine residue at position 48, 49, and/or 51) can be substituted with a non-conservative amino acid residue (e.g., glutamic acid) or a conservative or amino acid residue. Exemplary amino acids that can be substituted at a residue identified herein (e.g., position 48, 49, and/or 51) include glutamic acid, aspartic acid, and alanine.

Examples of variant neublastin polypeptides that exhibit reduced or absent heparin binding are disclosed in Table 1. Amino acid residues of the variant neublastin polypeptides that are mutated as compared to the corresponding wild type position are bolded and underlined. In addition, the neublastin polypeptide (113, 99, or 104 amino acids in length) used as the background for the substitution is depicted in Table 1.

TABLE 1

Variant Neublastin Polypeptides

| SEQ ID NO | Position Substituted | Length of Polypeptide | Amino Acid Sequence |
|---|---|---|---|
| 2 | Arg 48 | 113 | AGGPGSRARAAGARGCRLRSQLVPVRALGLGHRSDELVRFRFCSGSCERARSPHDLSLASLLGAGALRPPPGSRPVSQPCCRPTRYEAVSFMDVNSTWRTVDRLSATACGCLG |
| 3 | Arg 49 | 113 | AGGPGSRARAAGARGCRLRSQLVPVRALGLGHRSDELVRFRFCSGSCREARSPHDLSLASLLGAGALRPPPGSRPVSQPCCRPTRYEAVSFMDVNSTWRTVDRLSATACGCLG |
| 4 | Arg 51 | 113 | AGGPGSRARAAGARGCRLRSQLVPVRALGLGHRSDELVRFRFCSGSCRRAESPHDLSLASLLGAGALRPPPGSRPVSQPCCRPTRYEAVSFMDVNSTWRTVDRLSATACGCLG |
| 5 | Arg 48 and Arg 49 | 113 | AGGPGSRARAAGARGCRLRSQLVPVRALGLGHRSDELVRFRFCSGSCEEARSPHDLSLASLLGAGALRPPPGSRPVSQPCCRPTRYEAVSFMDVNSTWRTVDRLSATACGCLG |
| 6 | Arg 48 and Arg 49 | 99 | GCRLRSQLVPVRALGLGHRSDELVRFRFCSGSCEEARSPHDLSLASLLGAGALRPPPGSRPVSQPCCRPTRYEAVSFMDVNSTWRTVDRLSATACGCLG |
| 7 | Arg 48 and Arg 49 | 104 | AAGARGCRLRSQLVPVRALGLGHRSDELVRPRFCSGSCEEARSPHDLSLASLLGAGALRPPPGSRPVSQPCCRPTRYEAVSFMDVNSTWRTVDRLSATACGCLG |
| 8 | Arg 49 and Arg 51 | 113 | AGGPGSRARAAGARGCRLRSQLVPVRALGLGHRSDELVRFRFCSGSCREAESPHDLSLASLLGAGALRPPPGSRPVSQPCCRPTRYEAVSFMDVNSTWRTVDRLSATACGCLG |
| 9 | Arg 48 and Arg 51 | 113 | AGGPGSRARAAGARGCRLRSQLVPVRALGLGHRSDELVRFRFCSGSCERAESPHDLSLASLLGAGALRPPPGSRPVSQPCCRPTRYEAVSFMDVNSTWRTVDRLSATACGCLG |

A neublastin polypeptide can be optionally coupled to a polymer (e.g., a polyalkylene glycol moiety such as a polyethylene glycol moiety). In some embodiments, the polymer is coupled to the polypeptide at a site on the neublastin polypeptide that is an N terminus. In some embodiments, a variant neublastin polypeptide includes at least one amino acid substitution with respect to SEQ ID NO:1 (or with respect to amino acids 15-113 of SEQ ID NO:1), which provides an internal polymer conjugation site to which a polymer can be conjugated. In some embodiments, the polymer is coupled to a variant neublastin polypeptide at a residue (numbered in accordance with the sequence of SEQ ID NO:1) selected from the group consisting of position 14, position 39, position 68, and position 95. Exemplary neublastin variants that provide internal polymer conjugation sites are described in WO 02/060929 and WO 04/069176 (the contents of which are incorporated herein by reference).

A polypeptide can optionally contain heterologous amino acid sequences in addition to a neublastin polypeptide. "Heterologous," as used when referring to an amino acid sequence, refers to a sequence that originates from a source foreign to the particular host cell, or, if from the same host cell, is modified from its original form. Exemplary heterologous sequences include a heterologous signal sequence (e.g., native rat albumin signal sequence, a modified rat signal sequence, or a human growth hormone signal sequence) or a sequence used for purification of a neublastin polypeptide (e.g., a histidine tag).

Neublastin polypeptides can be isolated using methods known in the art. Naturally occurring or recombinantly produced neublastin polypeptides can be isolated from cells or tissue sources using standard protein purification techniques. Alternatively, mutated neublastin polypeptides can be synthesized chemically using standard peptide synthesis techniques. The synthesis of short amino acid sequences is well established in the peptide art. See, e.g., Stewart, et al., Solid Phase Peptide Synthesis (2d ed., 1984).

In some embodiments, neublastin polypeptides are produced by recombinant DNA techniques. For example, a nucleic acid molecule encoding a neublastin polypeptide can be inserted into a vector, e.g., an expression vector, and the nucleic acid can be introduced into a cell. Suitable cells include, e.g., mammalian cells (such as human cells or CHO cells), fungal cells, yeast cells, insect cells, and bacterial cells (e.g., *E. coli*). When expressed in a recombinant cell, the cell is preferably cultured under conditions allowing for expression of a neublastin polypeptide. The neublastin polypeptide can be recovered from a cell suspension if desired. As used herein, "recovered" means that the mutated polypeptide is removed from those components of a cell or culture medium in which it is present prior to the recovery process. The recovery process may include one or more refolding or purification steps. Buffers and methods for inducing folding of a denatured neublastin polypeptide are described in, e.g., PCT Application Number PCT/US2005/029638.

Variant neublastin polypeptides can be constructed using any of several methods known in the art. One such method is site-directed mutagenesis, in which a specific nucleotide (or, if desired a small number of specific nucleotides) is changed in order to change a single amino acid (or, if desired, a small number of predetermined amino acid residues) in the encoded variant neublastin polypeptide. Many site-directed mutagenesis kits are commercially available. One such kit is the "Transformer Site Directed Mutagenesis Kit" sold by Clontech Laboratories (Palo Alto, Calif.).

Pharmaceutical Compositions

A neublastin polypeptide can be incorporated into a pharmaceutical composition containing a therapeutically effective amount of the polypeptide and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., REMINGTON'S PHARMACEUTICAL SCIENCES (Maack Publishing Co., Easton, Pa.).

Administration of a pharmaceutical composition containing a neublastin polypeptide can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration. Administration can be to the peripheral nervous system and/or the central nervous system (CNS).

Administration may be by periodic injections of a bolus of the pharmaceutical composition or may be made more continuous by intravenous or intraperitoneal administration from a reservoir which is external (e.g., an IV bag) or internal (e.g., a bioerodable implant, a bioartificial organ, or a colony of implanted neublastin production cells). See, e.g., U.S. Pat. Nos. 4,407,957, 5,798,113, and 5,800,828, each incorporated herein by reference.

In particular, administration of a pharmaceutical composition may be achieved using suitable delivery means such as: a pump (see, e.g., Annals of Pharmacotherapy, 27:912 (1993); Cancer, 41:1270 (1993); Cancer Research, 44:1698 (1984), incorporated herein by reference); microencapsulation (see, e.g., U.S. Pat. Nos. 4,352,883; 4,353,888; and 5,084,350, herein incorporated by reference); continuous release polymer implants (see, e.g., Sabel, U.S. Pat. No. 4,883,666, incorporated herein by reference); macroencapsulation (see, e.g., U.S. Pat. Nos. 5,284,761, 5,158,881, 4,976,859 and 4,968,733 and published PCT patent applications WO92/19195, WO 95/05452, each incorporated herein by reference); naked or unencapsulated cell grafts to the CNS (see, e.g., U.S. Pat. Nos. 5,082,670 and 5,618,531, each incorporated herein by reference); injection, either subcutaneously, intravenously, intra-arterially, intramuscularly, or to other suitable site; or oral administration, in capsule, liquid, tablet, pill, or prolonged release formulation.

In one embodiment, a pharmaceutical composition is delivered directly into the CNS (e.g., the brain ventricles, brain parenchyma, or the intrathecal space). The pharmaceutical composition can be delivered intrathecally.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch.

A pharmaceutical composition containing a neublastin polypeptide can optionally be administered to a subject within a specified period of time following damage or injury to nerve tissue (e.g., a dorsal root crush or a crush of a nerve distal to the dorsal root ganglia). For example, the pharmaceutical composition can be administered to the subject within, e.g., 1, 2, 3, 4, 5, 6, 7, 8, 9, 10, 11, 12, 13, 14, 21, 28, 35, 42, 49 or 56 days following damage or injury. The subject can be administered a single dose or multiple doses (e.g., 2, 3, 4, 5, 6, 7, or more doses) of the pharmaceutical composition. Administrations of multiple doses can be separated by intervals of hours, days, weeks, or months.

Formulations suitable for parenteral administration conveniently contain a sterile aqueous preparation of the neublastin polypeptide, which preferably is isotonic with the blood of the recipient (e.g., physiological saline solution). Formulations may be presented in unit-dose or multi-dose form.

An exemplary formulation contains a neublastin polypeptide described herein and the following buffer components: sodium succinate (e.g., 10 mM); NaCl (e.g., 75 mM); and L-arginine (e.g., 100 mM).

Formulations suitable for oral administration may be presented as discrete units such as capsules, cachets, tablets, or lozenges, each containing a predetermined amount of the neublastin polypeptide; or a suspension in an aqueous liquor or a non-aqueous liquid, such as a syrup, an elixir, an emulsion, or a draught.

Therapeutically effective amounts of a pharmaceutical composition may be administered to a subject in need thereof in a dosage regimen ascertainable by one of skill in the art. For example, a composition can be administered to the subject, e.g., systemically at a dosage from 0.01 µg/kg to 1000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a neublastin polypeptide is first administered at different dosing regimens. The unit dose and regimen depend on factors that include, e.g., the species of mammal, its immune status, the body weight of the mammal. Typically, protein levels in tissue are monitored using appropriate screening assays as part of a clinical testing procedure, e.g., to determine the efficacy of a given treatment regimen.

The frequency of dosing for a neublastin polypeptide is within the skills and clinical judgement of physicians. Typically, the administration regime is established by clinical trials which may establish optimal administration parameters. However, the practitioner may vary such administration regimes according to the subject's age, health, weight, sex and medical status. The frequency of dosing may be varied depending on whether the treatment is prophylactic or therapeutic.

Methods of Treatment

The neublastin polypeptides described herein can be used for treating impaired proprioception, treating brachial plexus injuries, regenerating large and small nerve fibers, promoting reentry of nerve fibers through the DREZ into the spinal cord, and/or improving sensory neural responses.

1. Treatment of Impaired Proprioception

The neublastin polypeptides disclosed herein (and pharmaceutical compositions comprising same) can be used in methods for treating impaired proprioception.

Impaired proprioception inhibits properly coordinated muscular effort and results in an altered perception of body-space relation. In humans, loss of proprioception often occurs as a result of nerve trauma or damage (e.g., damage resulting from an injury). Injuries that can be associated with subsequent loss or impairment of proprioception include, e.g., stroke-related nerve damage or other ischemia-related neural injury, surgery, whiplash, concussions, cervical myelopathy (e.g., due to cervical stenosis), and injuries related to scoliosis (e.g., idiopathic scoliosis). Impairment can also result from complications due to diabetes or cancer (e.g., inflammation or injury due to an invasive tumor) or can result from tissue injury resulting from exposure to cytotoxic factors such as chemotherapy. Homeostatic proprioception can be impaired following use of peripheral or central nerve blocks, for example, during a surgical procedure.

Loss or impairment of proprioception can also occur from conditions not involving direct tissue damage or injury.

Patients who suffer from, for example, joint hypermobility or Ehlers-Danlos Syndrome (a genetic condition that results in weak connective tissue throughout the body) can present with impaired proprioception. Proprioception can also be temporarily or permanently impaired from certain viral infections. In some cases, temporary loss or impairment of proprioception may happen periodically during growth such as growth during adolescence. Other types of growth that could affect proprioception in a patient include, e.g., large gains or reductions in bodyweight/size due to fluctuations of fat and muscle content. Proprioceptive loss can also present in subjects who gain new levels of flexibility, stretching, and contortion, for example, a limb experiencing a new range of motion after a prolonged immobilization. In rare cases, temporary impairment of proprioception has also been known to occur following an overdose of vitamin B6 (pyridoxine and pyridoxamine).

Loss or impairment of proprioception can affect the upper extremities, lower extremities, or both, depending on the location and/or nature of the causative injury or condition. For example, an injury to the lower spine may only affect proprioception from the torso downward, whereas an injury to the upper portions of the spine can result in impaired proprioception in both upper and lower extremities.

Following administration of neublastin to a subject (e.g., a human), the efficacy (improvement) of the treatment on impaired proprioception can be assessed by comparing the subject's proprioception before and after treatment. Post-treatment assessment can occur immediately or shortly after treatment (e.g., 6, 12, 18, or 24 hours after treatment) and/or can occur days, weeks, or months following treatment. Where progression of the improvement of impaired proprioception following one or more neublastin treatments is to be assessed, a subject's proprioception can be evaluated or measured at multiple time points following neublastin treatment (e.g., a one day, two day, and one week evaluation; a one week, one month, and six month evaluation; a one month, six month, and one year evaluation).

Suitable methods of evaluating or measuring proprioception in a subject are known in the art. Where upper extremity proprioception is evaluated, examples of such evaluation methods include detection of joint motion (e.g., Cook et al. (1986) Clin. Orthop. Relat. Res. 213:118-24) and passive position matching tests using devices described in, e.g., Swanik et al. (1996) J Athl Train. 31(2):119-24 and Ulkar et al. (2004) Br. J. Sports Med. 38:549-52. In addition, upper extremity deficits in proprioception can be tested in humans using, e.g., the field sobriety test, wherein a subject attempts to touch the nose with the eyes closed. Subjects with normal proprioception generally make errors of no more than 2 cm. Subjects with severely impaired proprioception cannot perceive the location of their hands (or noses) without looking.

Where lower extremity proprioception is evaluated (e.g., hip or knee proprioception), proprioception can be assessed following a test for patient joint-position sense (Takayama et al. (2005) Spine 30(1):83-86) or measured using a manual protractor or electrogoniometer (Mendelsohn et al. (2004) Am. J. Phys. Med. Rehabil. 83(8):624-32). Lower extremity deficits in proprioception can also be determined by measuring static and dynamic balance. Proprioception of the spine can also be measured. Examples of such methods and devices are described in Christensen (1999) J Manipulative Physiol. Ther. 22(1):10-14 and U.S. Pat. No. 6,969,360.

The measurement or evaluation of proprioception in a patient can be quantitative or generally qualitative, e.g., a survey given to a patient where he or she rates the severity or extent of an altered perception as described in Klein et al. (2003) Reg. Anesth. Pain Med. 28(5):433-38. Additional proprioception tests are described in, e.g., Lee et al. (2003) Clin. Biomech. 18(9):843-47 and al-Othman et al. (1998) Orthopedics 21(6):677-79.

The Examples contained herein describe several assays useful for measuring proprioception in non-human model systems. Animal models of impaired proprioception are generally injury-related impaired proprioception models. Injuries can include, for example, unilateral C4-T2 dorsal root crush (Ramer et al. (2000) Nature 403:312-316). Additional suitable animal models of proprioception are described, for example, in Gaviria et al. (2002) J. Neurotrauma 19(2):205-221.

2. Treatment of Brachial Plexus Injuries

As described in the Examples, administration of neublastin to a mammal can result in restoration of sensorimotor function following nerve injuries to the brachial plexus. Brachial plexus injuries are caused by damage (injury) to the brachial plexus, a network of peripheral nerves (the C5, C6, C7, C8 and T1 nerves, in humans) that travel from the spine to the shoulder, arm, and hand. Symptoms of brachial plexus injuries can include a limp or paralyzed arm, lack of muscle control in the arm, hand, or wrist, and lack of feeling or sensation in the arm or hand. The neublastin polypeptides disclosed herein (and pharmaceutical compositions comprising same) can be used in methods of treating brachial plexus injuries in a subject (e.g., a human).

Brachial plexus nerves can be stretched, avulsed, or ruptured due to large amounts of stress put on the neck. Adults may suffer brachial plexus injuries through severe physical trauma such as an automobile or motorcycle accident (e.g., following a whiplash injury). Many brachial plexus injuries occur in ulero or at birth when a baby's shoulders become impacted causing the brachial plexus nerves to stretch or tear.

There are four types of brachial plexus injuries: (i) neuropraxia (stretch), in which the nerve has been damaged but not torn; (ii) avulsion, in which the nerve is torn from the spine; (iii) rupture, in which the nerve is torn but not at the spinal attachment; and (iv) neuroma, in which the nerve has attempted to heal itself but scar tissue has grown around the injury, placing pressure on the injured nerve and preventing the nerve from conducting signals to the muscles. Neuropraxia is the most common type of brachial plexus injury and can result in permanent and severe impairment of sensory function within the shoulder, arm, and hand.

Following administration of neublastin to a subject (e.g., a human), the efficacy (improvement) of the treatment on the brachial plexus injury can be assessed by comparing the extent or severity of a subject's injury before and after treatment. The efficacy of neublastin treatment on a brachial plexus injury can be assessed as a monotherapy or as part of a multi-therapeutic regimen. For example, neublastin can be administered in conjunction with other clinically relevant treatments for brachial plexus injury including, neurolysis (to remove scar tissue), muscle transfer, nerve grafts, or nerve reconstructive surgery.

Multiple modalities can be used to assess the extent or severity of a brachial plexus injury, including clinical examination, electrodiagnostic studies (e.g., electromyography (EMG), nerve conduction velocity (NCV), sensory nerve action potential (SNAP), and somatosensory evoked potential (SSEP)) and imaging studies (e.g., Computed Tomography (CT) Image Scan, Magnetic Resonance Imaging (MRI)) (Harper (2005) Hand. Clin. 21(1):39-46). These modalities can be used alone or in combination, the combination often delineating specific elements of the brachial plexus that have been injured and more detailed information about the severity of the injury. Clinical examination can include, but is not limited to, qualitative motor function evaluations that score both individual muscle groups (using the five-point British Research Council Grading System) and semi-quantitative or quantitative methods such as functional muscle group activities, including abduction, external rotation, and hand-to-head, hand-to-back and hand-to-mouth movements as well as sensory and reflex exams. Examples of sensory exams include, for example, The Thermal Threshold Testing System (Somedic, Stockholm, Sweden) described in Anand et al. (2002) Brain 125:113-22.

The unilateral C4-T2 dorsal root crush (as described in Ramer et al. (2000) Nature 403:312-16) damages nerves of the brachial plexus and is a useful rat model system for studying brachial plexus injury. Additional suitable animal models of brachial plexus injury are also described in, e.g., Quintao et al. (2006) Neuropharmacology 50(5):624-20; Rodrigues-Filho et al. (2003) Brain Res. 982(2):186-94; and Rodrigues-Filho et al. (2004) Brain Res. 1018(2):159-70. Methods used to evaluate the efficacy of a treatment (e.g., administering to a subject a neublastin polypeptide) on a brachial plexus injury are similar to those described for human patients and include, e.g., evaluating changes in temperature threshold or changes in nerve potential.

3. Regeneration of Large and Small Nerve Fibers and Promoting Reentry of Nerve Fibers Through the DREZ into the Spinal Cord As detailed in the Examples, systemic administration of neublastin was found to promote regeneration of nerve fibers, including axonal regeneration crossing the DREZ into the spinal cord as well as regeneration of injured nerve fibers distal to the dorsal root ganglia (DRG). Thus, the neublastin polypeptides disclosed herein (and pharmaceutical compositions containing same) can be useful in methods for regenerating, lost, damaged, or injured large (e.g., large myelinated or unmyelinated) and/or small (e.g., small myelinated or unmyelinated) fibers of the nervous system. Administration of a neublastin polypeptide can be useful for regenerating large and small fibers of the central nervous system (e.g., brain or spinal cord) as well as the peripheral nervous system (e.g., nerves of limbs, phalanges, face, skin, or tongue).

Types of nerve damage that can benefit from long and/or small nerve fiber regeneration and can be treated by administration of a neublastin polypeptide generally include instances where one or more nerves are injured (e.g., crushed) or severed. The nerve damage can occur as a result of a nerve-damaging infection (e.g., a bacterial or viral meningitis, bacterial, viral, or protozoal encephalitis, or polio) or diseases (e.g., hereditary, sporadic, or ideopathic diseases) such as multiple sclerosis, Gillain Barre syndrome, diabetes, Charcot-Marie-Tooth disease, Friedrich's ataxia, Bell's palsy, or spina bifida. Nerve injuries that can benefit from administration of neublastin also include those resulting from fractures, strains, or breakages of bones (or tendons or ligaments), electrical shock, exposure to certain toxic chemicals (e.g., solvents, heavy metals, or nitrous oxide), certain types of burns, skin or other tissue grafting, acute compression (e.g., nerve entrapment such as ulner nerve entrapment or carpal tunnel syndrome), or nerve damage resulting from surgery other medical procedures (e.g., lingual nerve injury following tooth extraction). Additional nerve damage that can be treated using any of the neublastin compositions described herein includes damage occurring as a result of, e.g., Parkinson's disease, amyotrophic lateral sclerosis, or nerve-damaging injury or inflammation associated with Alzheimer's disease or other tauopathies, sub-acute-sclerosing panencephalitis, progressive multifocal leuco-encephalopathy, or any of the prion-type spongioform encephalopathies.

Following administration of neublastin to a subject (e.g., a human), the efficacy of the treatment in promoting nerve regeneration can be assessed by comparing the state or function of the subject's nerve(s) before and after treatment. The efficacy of neublastin treatment on nerve regeneration can be assessed as a monotherapy or as part of a multi-therapeutic regimen. For example, neublastin can be administered in conjunction with other clinically relevant treatments for nerve regeneration including, but not limited to, physical therapy, hyperbaric treatments, light-activated nerve regeneration (laser or light emitting diode), or medicaments such as methylprednisolone.

The regeneration of large or small nerve fibers can be assessed in a subject (e.g., a human) by direct analysis of one or more nerves using, for example, nerve conduction velocity recordings, the Pressure-Specified Sensory Device™ (Sensory Management Services, LLC, Baltimore Md.), or imaging techniques such as those described above. In some cases, for example where regeneration is of the central nervous system, nerve regeneration can be evaluated as an increase in white matter volume (e.g., nerve mass of the spine or brain), particularly where the damage or disorder has resulted in nerve atrophy, using, e.g., magnetic resonance spectroscopy scans. Peripheral nerve regeneration can be directly assessed by biopsy and/or ex vivo electrophysiological techniques as described in, e.g., Polydefkis et al. (2004) Brain 127(7):1606-15.

Where nerves of the skin have been damaged (e.g., damage from a cutaneous burn or severed nerves of grafted skin), the regeneration of nerves of the skin (e.g., nerve reinnervation) following administration of a neublastin polypeptide can be assessed using a variety of methods known in the art. For example, one or more sensory functions (e.g., sensitivity of the skin) can be measured using sensory nerve action potential (SNAP) measurements or sympathetic skin response (SSR) tests as described in, e.g., Beneke et al. (1980) J Neurol. 223(4):231-39, Jazayeri et al. (2003) Electromyogr. Clin. Neurophysiol. 43(5):277-79, Huang et al. (2004) Chin. Med. J (Engl) 117(9):1317-20, or Pan et al. (2006) Arch. Phys. Med. Rehabil. 87(9):1201-06. Skin reinnervation following administration of neublastin can also be assessed in a patient by monitoring a change in responsiveness to mechanical or heat stimuli or to sympathetic reflex provocation tests, such as those described in Schmelz et al. (1998) J Neurophysiol. 79(4):1653-1660.

Alternatively (or in addition), nerve regeneration can be measured "functionally," e.g., by measuring an improvement of impaired proprioception through regeneration of the injured nerve. Assessment methodologies for nerve regeneration can also include any of the evaluation methods for any of the nerve-related injuries described herein.

The Examples describe animal models useful for studying the effect of a neublastin treatment on nerve regeneration. The efficacy of such treatment in animal models can be evaluated by direct analysis of the nerves, for example, by immunohistochemistry techniques on a biopsy or tissue section. Alternatively, nerve regeneration can be detected as restoration of sensation or motor activity following regeneration of the nerves. Additional animal models for studying the effects of a treatment on nerve regeneration include, for example, those described in Oudega et al. (1996) 140(2):218-29, Frykman et al. (1998) Orthop. Clin. North. Am.

19(1):209-19, Zhang et al. (2005) Adv. Biochem. Eng. Biotechnol. 94:67-89, and Pan et al. (2003) J. Neurosci. 23(36):11479-88.

4. Improvement of Sensory Neural Responses

As described in the Examples, administration of neublastin to a mammal with a nerve injury results in restoration of lost sensory-neural responses and sensorimotor functions. Thus, administration to a subject (e.g., a human) of a neublastin polypeptide described herein can be useful in restoring sensation and/or sensorimotor functions in the subject. Such sensory-neural responses can include, for example, response to sensation of pressure, temperature, and vibration (see Toibana et al. (2000) Industrial Health 38:366-371). Sensorimotor functions control, e.g., balance, equilibrium, and coordination (e.g., coordination of limb motion).

Loss of sensory-neural responses/sensorimotor function can result from damage or trauma to one or more nerves, the causes of nerve damage or trauma including any of those described herein. For example, loss or impairment of a sensory response can result from complications due to diabetes or from desensitization following exposure to extreme heat (e.g., a burn). Following administration of neublastin to a subject, the efficacy of the treatment in improving sensory neural responses can be assessed by comparing the subject's sensory nerve response(s) before and after treatment. The efficacy of neublastin treatment in improving sensory neural responses can be assessed as a monotherapy or as part of a multi-therapeutic regimen as described above. For example, neublastin can be administered in conjunction with other clinically relevant treatments for improving sensory neural responses, or in conjunction with any other treatment modality described herein (e.g., a treatment for the nerve damage or injury).

Methods of assessing an improved sensory-neural response in a human subject following treatment are numerous and include, e.g., electromyographic nerve conduction (EMG-NCV) tests and sensory nerve perception threshold testing (also referred to as current perception threshold testing), which involves quantification of a sensory threshold to transcutaneous electrical stimulation (the minimal amount of transcutaneous electrical stimulation required to evoke a sensation in a subject). Additional methods of assessing sensorimotor function in a human subject include, for example, pinch and grip strength (Dellon et al. (1997) Ann Plat. Surg. 38(5):493-502), angle reproduction tests (see above), threshold-to-motion tests, isometric strength testing, Romberg's Test, flexion reflexes (Hornby et al. (2003) J Neurophysiol. 89(1):416-26), and tests for hand-eye coordination.

Touch sensation can be assessed, for example, by gently rubbing a ball of cotton on the surface of the skin of the region tested, or gently applying pressure to various locations of the region. These types of sensory nerve perception threshold assessments are useful in evaluating a wide range of clinical conditions including central and peripheral neuropathies and detection of carpal tunnel syndrome, and can involve the use of devices such as the Neurometer Current Perception Threshold (Neurotron, Inc., Baltimore, Md.) or the Medi-Dx 7000 (Vax-D Medical Group, Tucson, Ariz.). Additional descriptions of clinical tests and devices useful for assessing sensory neural responses can be found, e.g., in Shy et al. (2003) Neurol. 60:898-904 and Siao et al. (2003) Phys. Med. Rehabil. Clin. N. Am. 14(2):261-86. Methods of assessing sensory-neural or touch-sensation responses also include sensory nerve action potential (SNAP) measurements, sympathetic skin response (SSR) tests, and responsiveness to mechanical or heat stimuli or to sympathetic reflex provocation tests, such as those described above.

The Examples describe animal models for studying the effect of a treatment on improving sensory-neural responses/sensorimotor function. For example, following a nerve injury (e.g., a dorsal root crush or a crush of a nerve distal to the dorsal root ganglia), sensorimotor function in an animal can be evaluated with and without treatment (i.e., treatment with a neublastin polypeptide) by assessing an animal's performance in the stabilization maneuver. Additional animal models useful in measuring sensory-neural responses and/or sensorimotor function are described in, e.g., Diamond et al. (1992) J. Neurosci. 12(4):1467-76, Brown et al. (2005) J. Neurotrauma 22(5):559-74, and Magnuson et al. (2005) J. Neurotrauma 22(5):529-43.

The following are examples of the practice of the invention. They are not to be construed as limiting the scope of the invention in any way.

EXAMPLES

Example 1

Materials and Methods

Animal Surgery, Neublastin Administration, and Tracing Studies

Unilateral C4-T2 dorsal root crush (Ramer et al. (2000) Nature 403:312-16) was performed on male Sprague-Dawley rats (Harlan, Indianapolis, Ind.), weighing 175-250 grams. Sham surgery was processed under the same procedures without root injury. Rat neublastin (Gardell et al. (2003) Nat Med 9:1383-89) or saline vehicle was given subcutaneously on a Monday, Wednesday, and Friday schedule immediately after surgery for a total of 6 injections over 2 weeks. For transganglionic tracing, the median nerve branch of the brachial plexus was exposed under sterile conditions and a 5 μl solution of 0.5% CTB (Cholera Toxin B subunit, low salt; List Labs) was pressure injected into the nerve with multiple injection sites at 5-7 days before sacrifice.

Behavioral Observations

Behavioral assays for quantification of restoration of nociceptive, sensorimotor, and proprioceptive functions were performed according to the behavioral protocols described in Ramer et al. (2002) Mol Cell Neurosci 19:239-49 and Ramer et al. (2000) Nature 403:312-16. Paw withdrawal latency to noxious thermal stimulation was measured with a 49° C. water-bath, that is, the forepaw ipsilateral to injury was immersed in a 49° C. water-bath until the rat withdrew its paw or until the cut-off time of 20 seconds was reached. Ipsilateral forepaw withdrawal to noxious mechanical stimulation was tested with a Randall-Selitto noxious pinch device (Ugo-Basil) with the cutoff set at 250 grams. Scoring of rat performance in contact-evoked grasping, beam walking, horizontal ladder and stabilization placement was done as previously described (Ramer et al. (2002) Mol Cell Neurosci 19:239-49; and Ramer et al. (2000) Nature 403:312-16).

Immunohistochemistry

Rats were transcardially perfused with 10% buffered formalin (Sigma) and cervical spinal cord, DRG, and brainstems were removed, cryoprotected (in 20% sucrose), frozen, and sectioned (10 μm for DRG, 20 μm for spinal cord) on a cryostat. Sections were incubated with primary antibodies for CGRP (host rabbit/guinea pig, 1:10,000, Peninsula), $P2X_3$ (host rabbit/guinea pig, 1:10,000, Neuromics), NF200 (host mouse, 1:5,000, N52, Sigma), GFRα3 (R11, 2 µg/ml; Orozco wt al. (2001) Eur J Neurosci 13:2177-82), Ret (2 µg/ml; Orozco wt al. (2001) Eur J Neurosci 13:2177-82), GFAP (host mouse, 1:5,000, Sigma), ED1 (host mouse, 1:2,000, Serotec), FOS (host rabbit, 1:5,000, Calbiochem), CTB (host goat, 1:5,000, List Labs) and to NK1R (host rabbit, 1:5,000; Honore et al. (1999) J. Neurosci. 19:7670-78). Secondary antibodies were Cy3-conjugated goat antibody to rabbit IgG (1:1,000, Jackson), Alex fluor 488/594-conjagated goat antibodies to rabbit, mouse, or guinea pig IgG (1:1,000, Molecular Probes), and Alex fluor 594-conjagated donkey antibody to goat IgG (1:1,000, Molecular Probes). Immunoreactive cells and total cells (visualized with DAPI or ethidium bromide; Guo et al. (1999) Eur. J. Neurosci. 11:946-58) were counted on randomly selected sections. Quantitative analysis of axon density within the dorsal root along the central side of DREZ, as well as the density of immunoreactivity within spinal dorsal horn, was carried out as previously described (Ramer et al. (2000) Nature 403:312-16; and Wang et al. (2003) Neuroscience 121:815-24).

Nociceptive Reaction and FOS Expression in Formalin-Induced Inflammation

The experiments were performed in awake, freely moving rats as described previously (Presley et al. (1990) J Neurosci 10:323-35). The plantar surface of the ipsilateral forepaw of the rat that received dorsal root crush and neublastin/vehicle treatment was injected with 100 µl of 10% formalin subcutaneously, and the licking time on the injection site was recorded as previously described (Abbadie et al. (1992) Brain Res 578:17-25). Three hours after the injections, the rats were perfused, and C4-T2 spinal cord was harvested for immunohistochemistry to examine formalin induced FOS expression in the spinal dorsal horn. The control rats received the same amount of saline injections.

Mechanical Stimulation and NK1R Internalization in Carrageenan-Induced Inflammation The experiment was performed by the modified method described by Mantyh and colleagues (Honore et al. J. Neurosci. 19:7670-78). A subcutaneous injection of 100 µl of a suspension of 2% λ-carrageenan (Sigma-Aldrich, St. Louis, Mo.) in saline (pH 6.8) was administered into the plantar surface of the forepaw of the rat. After 3 hours, the rats were subjected to non-noxious mechanical stimulation by light stroking of the dorsal forepaw every second for 5 minutes with the wooden handle of a brush or to a noxious mechanical stimulation applied as a 30 second pinch with a hemostat applied to the distal part of the forepaw. The anesthetized rats were perfused for 15 minutes with phosphate-buffered saline followed by gluteraldehyde fixative for preparation for immunohistochemical visualization of internalization of the NK1 receptor in the spinal dorsal horn.

Electrophysiological Methods

Animals were maintained at surgical levels of isoflurane anesthesia for the duration of all terminal electrophysiology experiments. Experimenters were blinded as to treatment until all experiments in the set had been completed. The cervical cord was exposed from C4 to C8 and stabilized with spinal clamps on C2 and T2. Radial, median, and/or ulnar nerves were exposed just below the brachial plexus in both forelimbs and suspended on silver hooks for stimulation. Mineral oil was applied to keep the nerves and cord from drying out. A low-impedance metal microelectrode with a large 1 mm tip exposure (A-M Systems #563410) was vertically positioned 1 mm lateral to the cord midline and manually advanced to a depth approximately 0.5 mm from the ventral boundary (i.e., in the ventral horn). A second electrode was positioned in nearby muscles surrounding the cord and recordings were made differentially. A data acquisition board (National Instruments, PCI-6036E) triggered an electrical pulse-stimulator (A-M Systems Model 2100), which delivered single 50 ms monophasic square wave pulses of 0-8V amplitude at rates from 1-11 Hz to the peripheral nerves. Unless otherwise noted, the radial nerve was stimulated using pulses with amplitude of 4V delivered at an average rate of 2 Hz. Single responses were filtered (0.1 Hz-3 kHz), digitized (16 bits, 20 kHz sampling rate), averaged (typically, 50 traces) and stored for analysis off-line. The spinal preparation usually produced stable, replicable neuronal potentials for several hours. Recordings were made from the ventral horn at each segmental level (C4-C8) on both sides of the cord in response to ipsilateral stimulation of individual brachial nerves. Averaged cervical ventral root potentials in normal, unlesioned rats typically ranged from 100-300 µV in maximum amplitude (noise level typically ~10 µV), depending upon the individual animal, the nerve stimulated, and the rostrocaudal location of the recording electrode. The peak magnitude of the ventral horn field potential at 2-6 ms latency was adopted as a robust physiological measure of the summed short latency monosynaptic response in the cord at a given location. A further refinement of the estimation of monosynaptic response fits a standard model trace to a given response curve (Mears et al. (1994) Exp. Neurol. 130:115-19). The model trace has latency and exponential decay characteristics typical of excitatory post-synaptic currents generated by Ia-motoneuron synapses. The peak value of the fitted curve, usually very close to the raw peak magnitude, was then adopted as the estimate of the summed population monosynaptic response for stimulation of that segmental level and peripheral nerve. The maximum response observed amongst all recording sites was taken as the global estimate of synaptic function. This maximum response was deemed significantly larger than zero if its value was greater than 3 times the noise level, typically ~30 uV. To rule out possible false negative responses due to decline in the physiological state of the spinal cord, recordings were made first on the lesioned side of the cord and then on the unlesioned side, where the existence of normal responses ensured that the spinal cord was still functionally uncompromised.

Statistical Analysis

Statistical comparisons between treatment groups were done using ANOVA followed by Fisher Least Significant Difference test. Pairwise comparisons were made with Student t-test. Significance was set at $P=0.05$.

Example 2

Neublastin Promotes Axonal Regeneration into the Spinal Cord

N52, CGRP and P2X$_3$ immunolabelling was employed to visualize myelinated, unmyelinated peptidergic and unmyelinated "peptide-poor" fibers, respectively (Ramer et al. (2000) Nature 403:312-16). Together, these markers label nearly all DRG neurons (Bradbury et al. (1998) Mol. Cell. Neurosci. 12:256-68; Averill et al. (1995) Eur. J. Neurosci. 7:1484-94; and Bennett et al. (1998) J. Neurosci. 18:3059-72). Neublastin (1 mg/kg, subcutaneous administration) given on a Monday-Wednesday-Friday schedule for two consecutive weeks starting on the day of dorsal root crush (DRC) injury of the brachial plexus (the schedule used for Examples 2-8) elicited re-growth of both myelinated and unmyelinated axons through the DREZ. Sections from sham-operated animals showed uninterrupted immunofluorescent labeling for N52, CGRP and $P2X_3$ in axons from the periphery through the DREZ. Labeling for these markers terminated abruptly at the DREZ in DRC vehicle-treated rats. In contrast, sections from DRC neublastin-treated rats showed all the immunohistochemical markers central to the DREZ. Neublastin normalized DRC-induced reductions in immunolabeled axon densities (FIG. 2; Ramer et al. (2000) Nature 403:312-16). Moreover, in neublastin DRC tissues, immunofluorescence for CGRP and $P2X_3$ was found principally in the outer laminae of the dorsal horn whereas that for CTB was distributed throughout the outer and intermediate laminae, corresponding to the normal termination patterns of these fibers. Neublastin had no detectable effects in sham-operated animals.

Example 3

Systemic Neublastin Restores Nociceptive Functions

Figure 3A:
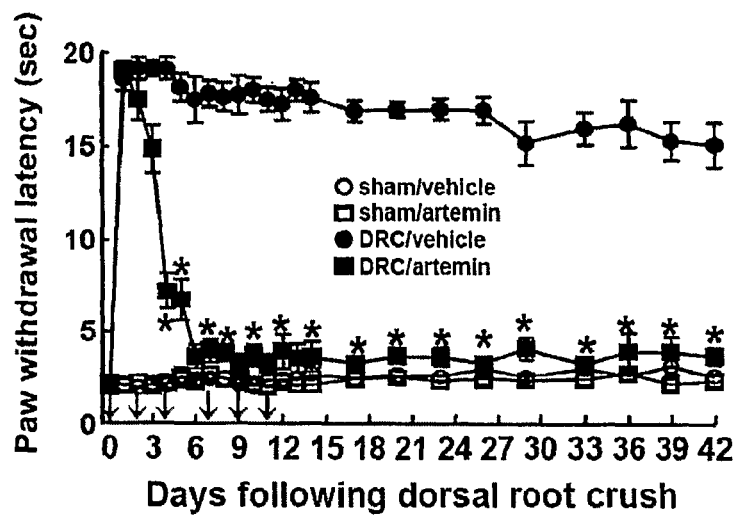
FIGS. 3A and 3B are graphs depicting the effect of systemic neublastin (artemin) administration on response to exposure of the forepaw to hot water (FIG. 3A) and to noxious mechanical stimuli (FIG. 3B) following DRC. Arrows indicate the time when each injection of neublastin or vehicle was made. Asterisks indicate behavioral responses significantly ($p \leq 0.05$) different from baseline values obtained prior to DRC.
Figure 3B:
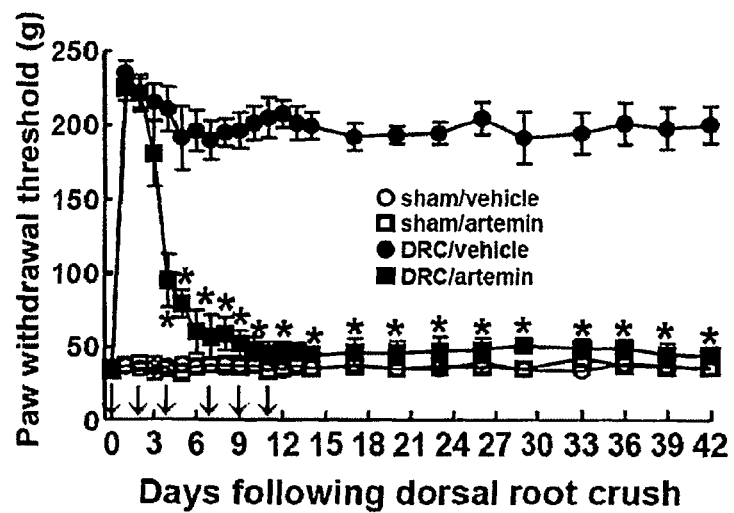
Figures 6A, 6B, 6C:
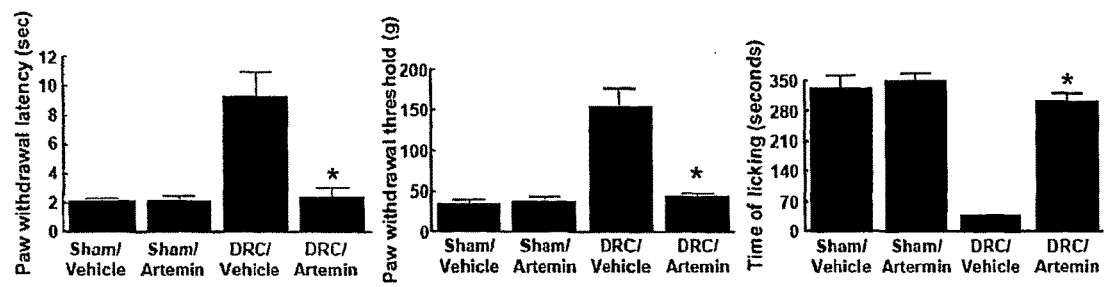
FIGS. 6A-6G are graphs depicting persistent functional recovery six months after DRC in systemic neublastin (artemin) treated rats: responses to noxious thermal, mechanical and chemical stimuli (FIGS. 6A-6C, respectively); and performance in placement stabilization, beam walking, horizontal ladder, and contact-evoked grasping (FIGS. 6D-6G, respectively). Asterisks indicate significant differences in behavioral responses of the neublastin-treated DRC group when compared to the vehicle-treated DRC group.

Withdrawal response to immersion of the forepaw ipsilateral to DRC or sham surgery in a 49° C. water bath or to noxious pressure was recorded. Animals with DRC injury and treated with vehicle showed marked insensitivity to both noxious heat or pressure with little change in responses throughout the 6 week evaluation (FIGS. 3A and 3B) and at 6 months after DRC (FIGS. 6A and 6B). Neublastin caused a progressive and rapid recovery of both thermal and mechanical thresholds in DRC rats. Responses to noxious stimuli were present within 4 days, and approached normal levels within 7 days of DRC (FIGS. 3A and 3B). Termination of neublastin treatment on day 11 did not affect restoration of nociceptive responses since they remained fully normalized over the entire 42 day observation period and also at the 6 month time-point (FIGS. 6A and 6B). Neublastin did not alter response thresholds in sham-operated groups at any time-point (FIGS. 3A and 3B and FIGS. 6A and 6B).

Example 4

Systemic Neublastin Restores Post-Synaptic Functions

Figure 3C:
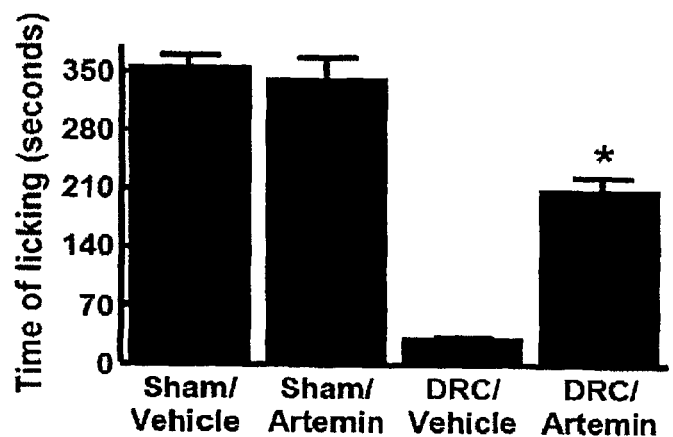
FIG. 3C is a graph depicting the effect of systemic neublastin (artemin) administration on licking responses, indicated by cumulative time spent licking a forepaw injected with formalin, following DRC. The asterisk indicates a significant ($p \leq 0.05$) difference in licking response relative to the group with DRC and vehicle treatment (DRC/vehicle).
Figure 3D:
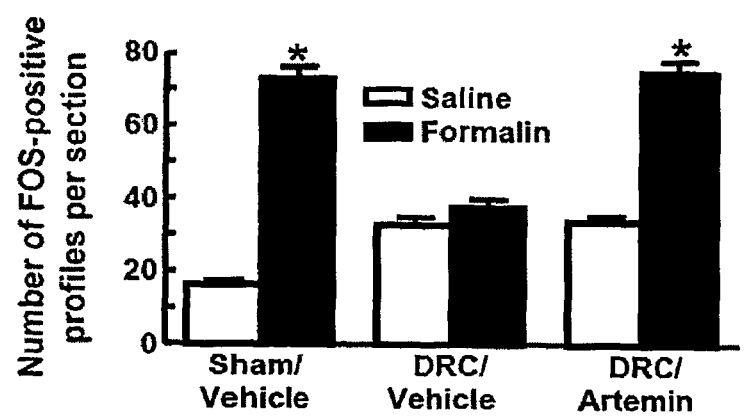
FIG. 3D is a graph depicting the effect of systemic neublastin (artemin) administration on FOS expression at day 14 in ipsilateral dorsal horn in response to formalin injection into the forepaw following DRC. The sham-operated group and the group that received DRC and neublastin (artemin) treatment both demonstrated significant ($p \leq 0.05$) increases in formalin-induced FOS expression, as indicated by the asterisks.

Noxious stimulus-induced expression of the proto-oncogene product FOS in the spinal dorsal horn is indicative of neuronal excitation of post-synaptic cells (Presley et al. (1990) J Neurosci 10:323-35; Hunt et al. (1987) Nature 328:632-34; and Harris (1998) Brain Res Bull 45:1-8). Forepaw formalin injection produced stereotypic licking behaviors along with increased numbers of FOS-positive spinal cord cell profiles (FIGS. 3C and 3D). DRC injury with vehicle treatment abolished both formalin-induced licking and evoked spinal FOS (FIGS. 3C and 3D). In contrast, neublastin preserved both the formalin-evoked behavioral and FOS responses at the day 14 (FIGS. 3C and 3D) and 6 month time points (FIG. 6C).

Figure 3E:
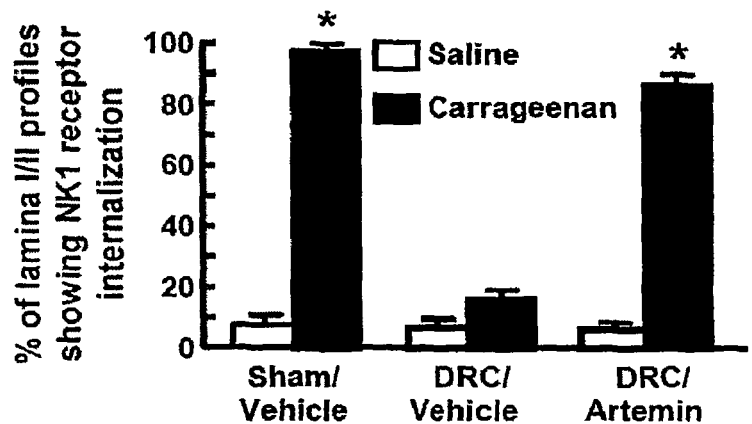
FIG. 3E is a graph depicting the effect of systemic neublastin (artemin) administration on internalization of NK1 receptors following a noxious mechanical pinch applied to rats with carrageenan-induced inflammation that had undergone DRC. Asterisks indicate significant differences from the non-inflamed (saline-treated) groups.
Figure 3F:
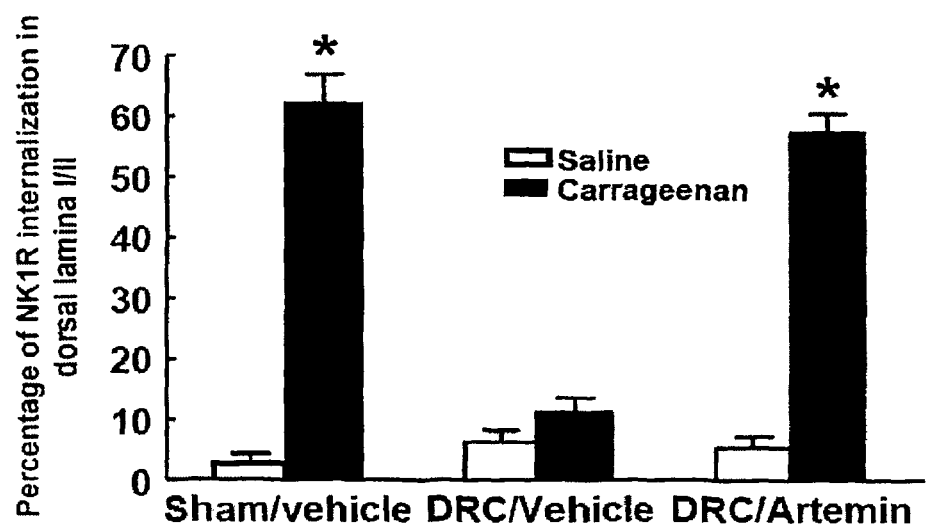
FIG. 3F is a graph depicting the effect of systemic neublastin (artemin) administration on NK1 receptor internalization in lamina I/II of dorsal horn following DRC. Asterisks indicate significant ($p \leq 0.05$) differences from the saline injected, uninframed group.

Evoked internalization of the NK1 receptor in the spinal dorsal horn by either noxious mechanical or by innocuous tactile stimuli in injured animals is indicative of post-synaptic responsiveness of dorsal horn neurons to substance P released from primary afferent fibers (Honore et al. J. Neurosci. 19:7670-78). Noxious pinch elicited internalization of the NK1 receptor in 96±2.6% of NK1-R positive dorsal horn profiles (FIG. 3E) and light brush following carrageenan injection caused internalization in 62±4.7% of the NK1R-positive profiles (FIG. 3F) in the outer lamina of the sham-operated animals. DRC injury reduced the pinch-evoked (FIG. 3E) and touch-evoked (FIG. 3F) internalization to 16±3.0% and 11±2.5% of the NK1R-expressing profiles, respectively. Neublastin treatment after DRC preserved the responses of post-synaptic dorsal horn neurons; noxious mechanical stimulation resulted in internalization of the NK1 receptor in 85±3.7% (FIG. 3E) and light brush caused internalization in 57±3.1% (FIG. 3F) of the NK1-expressing dorsal horn neurons, thus indicating a significant restoration of SP-NK-1 receptor synaptic responses. Neublastin treatment did not alter the responses of sham-operated animals in these studies.

Figure 4:
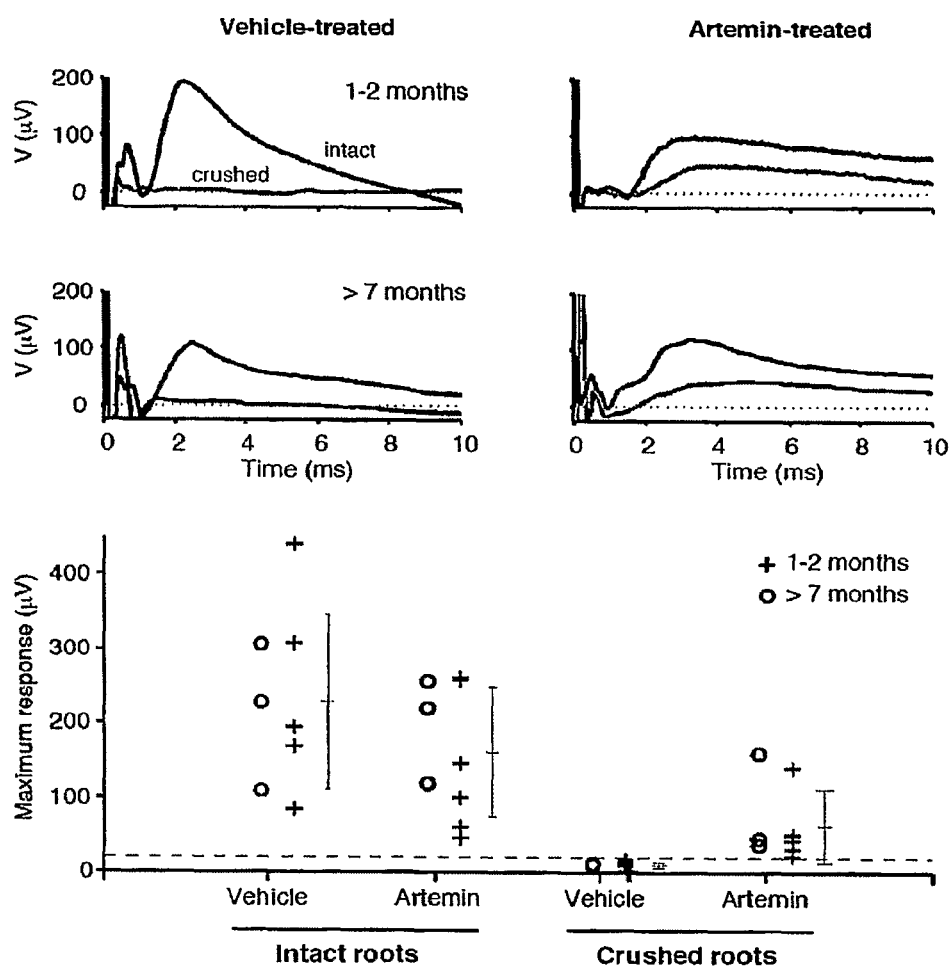
FIG. 4 (top) are graphs depicting traces of field potentials recorded extracellularly in the ventral spinal cord in response to electrical stimulation of the median or radial nerves in the ipsilateral forelimb. On the unlesioned side of experimental animals (intact roots), the synaptic responses began 1.0 to 1.5 ms after the stimulus, with rise-times of 1.0 to 1.5 ms, both in vehicle-treated and artemin-treated animals. In artemin-treated rats, there was substantial recovery of these synaptic inputs at 1.4 and 7.5 months after DRC. There was no significant recovery of synaptic function after DRC in vehicle-treated rats, even at 7.5 months.

Stimulation of the median nerve ipsilateral to DRC or sham-operation resulted in spinal cord field potentials within 1 ms of stimulation (FIG. 4, top panel). These field potentials are generated by volleys of action potentials in large myelinated cutaneous and proprioceptive axons in dorsal roots while those appearing 2 to 10 ms later represent monosynaptic excitatory post-synaptic potentials (EPSPs) evoked by the nerve stimulation (FIG. 4, bottom panel). The EPSPs were abolished following DRC and vehicle treatment. Five of 6 rats neublastin-treated rats showed clear EPSPs on the crush side, indicating that axons in the lesioned roots had regenerated and formed functioning synapses. In contrast, none of the 8 rats injected with vehicle showed appreciable recovery of synaptic potentials on the crush side. No significant differences were observed between maximal responses recorded on the intact side of neublastin-treated versus vehicle-treated animals.

Example 5

Systemic Neublastin Restores Sensorimotor Functions

Figure 5A:
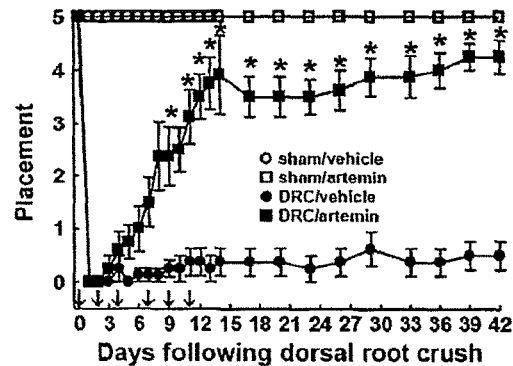
FIGS. 5A-5D are graphs depicting the effect of systemic neublastin (artemin) administration on recovery of the following sensorimotor functions over a 42 day observation period subsequent to DRC: placement/stabilization (FIG. 5A); ability to walk along a beam over an open area (FIG. 5B); numbers of foot slips when walking across a horizontal ladder (FIG. 5C); and contact-evoked grasping (FIG. 5D). Arrows indicate each injection of neublastin (artemin) or vehicle. Asterisks indicate significant ($p \leq 0.05$) differences in behavioral parameters relative to the first measurement taken after DRC or sham surgery.

Sensorimotor function was evaluated by the stabilization maneuver (Ramer et al. (2002) Mol. Cell. Neurosci. 19:239-49) in which the rat is nudged from behind and responds by placing the forelimbs in outstretched position, palms flat and toes outspread. Vehicle-treated rats with DRC consistently failed to respond with the stabilization maneuver (FIG. 5A). In contrast, the neublastin-treated rats showed a progressive recovery of the stabilization maneuver within 7 days, achieving nearly normal responses by day 14 and fully recovering, although more gradually, by 6 weeks (FIG. 5A) and remaining at normal levels at the 6 month observation point (FIG. 6D).

Figure 5B:
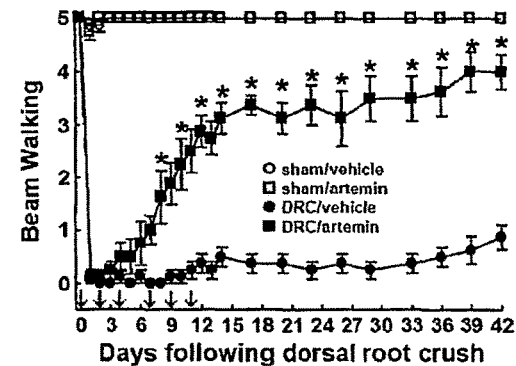
Figure 5C:
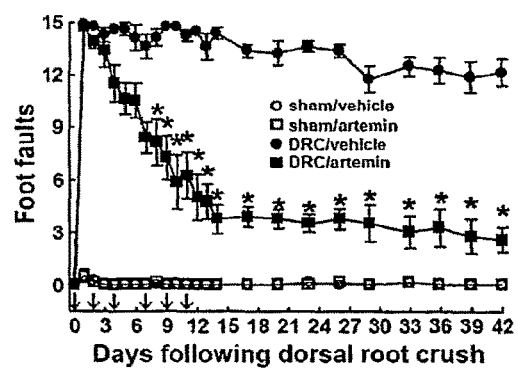

Impairment of sensory function, indicated by abnormal forelimb motion, impaired or inappropriate targeting, failure to bear weight or failure to use the forepaw entirely when walking on a 3-cm narrow beam (Ramer et al. (2002) Mol. Cell. Neurosci. 19:239-49) was graded from 0 (no limb use) to 5 (normal) by an observer blinded to the treatments. Animals with DRC injury showed complete disruption of limb use and scores were consistently less than 1 over the entire 42 day testing period (FIG. 5B). Neublastin produced a gradual, progressive improvement in beam-walking ability during the first 14 days, and continued improvement was noted beyond termination of neublastin injections (day 11), progressing at a slower rate over the remainder of the 42 day observation period (FIG. 5B) and normal 6 months later (FIG. 6E). Forelimb sensory deficit was further tested by allowing the rats to traverse a ladder oriented horizontally and counting the incidence of slipping of a forepaw from the ladder (Ramer et al. (2002) Mol. Cell. Neurosci. 19:239-49). Sham-operated animals rarely registered "foot-slips" while traversing the ladder whereas rats with DRC injury demonstrated an average of 14 incidents per trial (FIG. 5C). Neublastin treatment resulted in a gradual, progressive improvement in the ability of the rats to walk across the ladder (FIG. 5C).

Figures 6D, 6E:
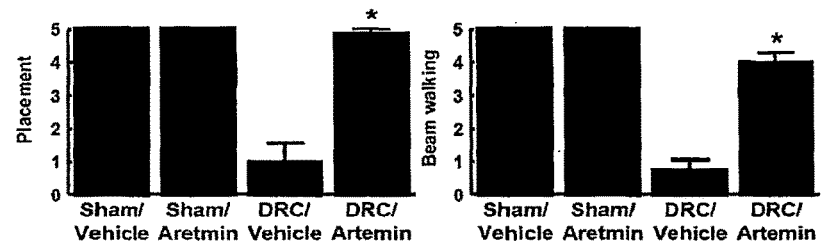
Figure 6F:
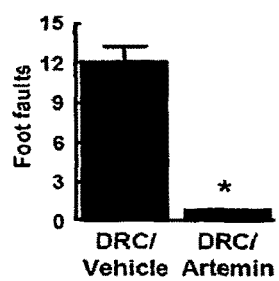

Improvement in sensorimotor function showed an apparent bi-phasic pattern, with rapid and very substantial improvement over the first 14 day period followed by a continued, but slower improvement of function over the remaining 42 days (FIGS. 5A-5C), reaching normal levels at the 6 month observation point (FIGS. 6D-6F). Neublastin treatment did not produce any changes in behavior of sham-operated rats (FIGS. 5A-5C and FIGS. 6D-6F).

Figure 5D:
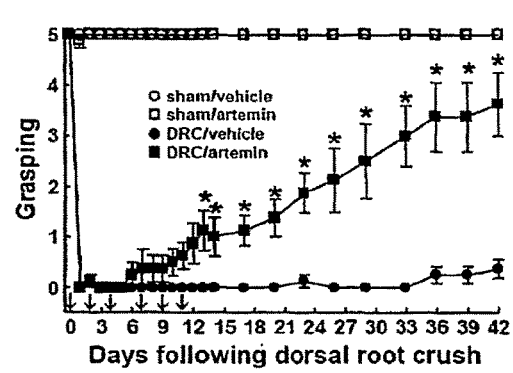
Figure 6G:
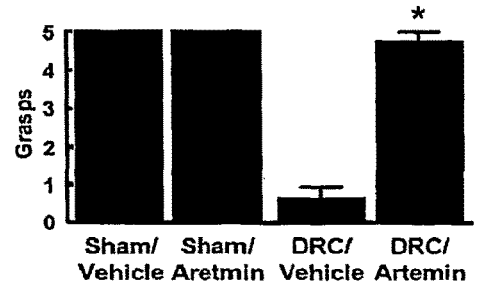

Contact-evoked grasping was used as a measure of a highly complex sensorimotor response that is organized at supraspinal levels (Ramer et al. (2002) Mol. Cell. Neurosci. 19:239-49). Sham-operated rats lowered towards a cage consistently grasped the lid. This response was completely abolished by DRC injury (FIG. 5D), and these rats would make forward-directed, waving-like movements of the forelimb, but grasping was never accomplished (Ramer et al. (2002) Mol. Cell. Neurosci. 19:239-49). Treatment with systemic neublastin produced a gradual, but consistently progressive, restoration of contact-evoked grasping (FIG. 5D) that was monophasic over the entire 42 day observation period. Contact-evoked grasping reached normal levels at the 6 month observation point (FIG. 6G).

Example 6

Systemic Neublastin Produces Long-Lasting Functional Recovery from Dorsal Root Injury Responses to nociceptive stimuli described above were largely abolished by DRC and remained absent 6 months after the injury (FIGS. 6A-6C) in vehicle treated animals. The essentially complete restoration of responses to noxious thermal, mechanical and chemical stimuli produced by neublastin treatment was still present 6 months after DRC (FIGS. 6A-6C) thus indicating the persistent restoration of normal nociceptive function by neublastin treatment. As described above, the neublastin-induced restoration of sensorimotor functions assessed by placement/stabilization, beam walking, horizontal ladder, and grasping tests was maintained 6 months after DRC (FIGS. 6D-6G). Neublastin did not change the behavioral responses of the sham-operated rats over the same time period. These data suggest that a limited schedule of neublastin treatment produces persistent restoration of sensorimotor function as well as responses to noxious stimuli.

Figure 6H:
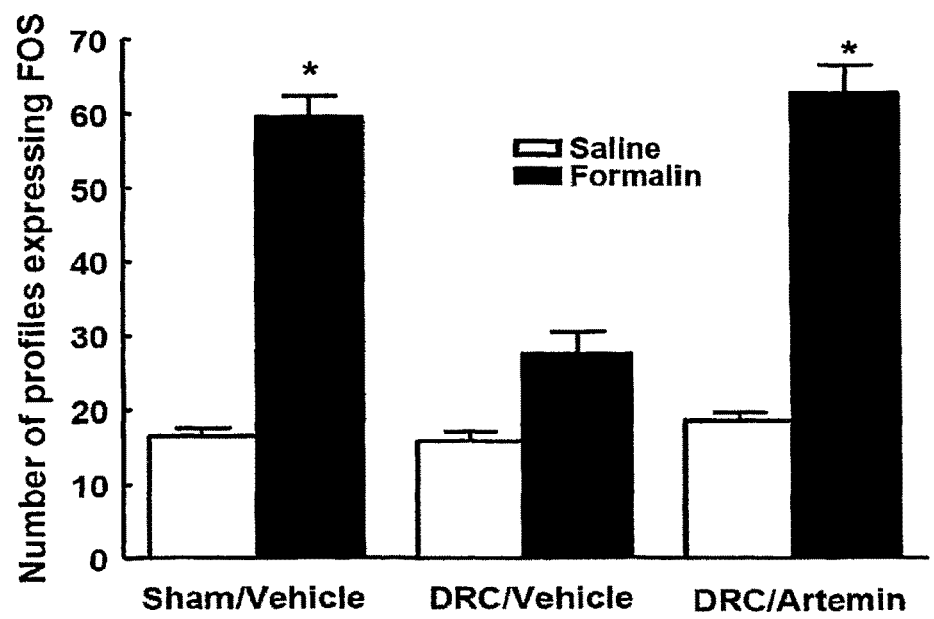
FIG. 6H is a graph depicting persistent recovery of postsynaptic FOS expression in the ipsilateral dorsal horn six months after DRC in systemic neublastin (artemin) treated rats. Asterisks indicate significant ($p \leq 0.05$) differences from the saline injected group.

Consistent with the persistent improvement in sensorimotor behavioral function, synaptic function was also maintained at these later times as shown by the recovery of formalin-evoked expression of FOS in the spinal dorsal horn (FIG. 6H). Additionally, three neublastin-treated rats were assessed electrophysiologically at 7-8 months post-lesion, and all 3 showed clear evidence of sensory-evoked EPSPs in the spinal cord. In contrast, none of the 3 vehicle-treated rats tested at this time point had measurable synaptic inputs (FIG. 4).

The neurochemical indices of regeneration of axons through the DREZ were consistent with the behavior observed 6 months after the injury. The restoration of immunofluorescent labeling for CGRP, $P2X_3$ and CTB into the spinal dorsal horn was still evident 6 months after DRC in the neublastin-treated animals, but was completely absent in spinal sections from vehicle-treated rats with DRC. Most striking was the appearance of labeling for CTB in the n. cuneatus 6 months after DRC in neublastin-treated, but not vehicle-treated, rats. This marker was not present in the n. cuneatus 14 days after the injury, suggesting that regeneration of myelinated afferent fibers to this supraspinal nucleus occurs over a prolonged time-course after injury and following neublastin treatment, consistent with the slow rate of restoration of complex sensorimotor behavior indicated by contact-evoked grasping.

Example 7

Figure 7A:
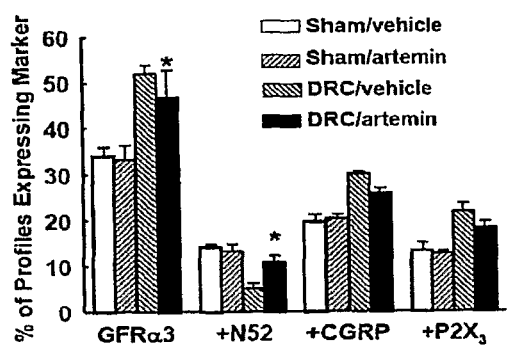
FIGS. 7A and 7B are graphs depicting the effect of systemic neublastin (artemin) administration on dorsal root ganglia neuronal profiles expressing N52, CGRP or $P2X_3$ and co-expressing either GFRα3 (FIG. 7A) or RET (FIG. 7B) 14 days after DRC.
Figure 7B:
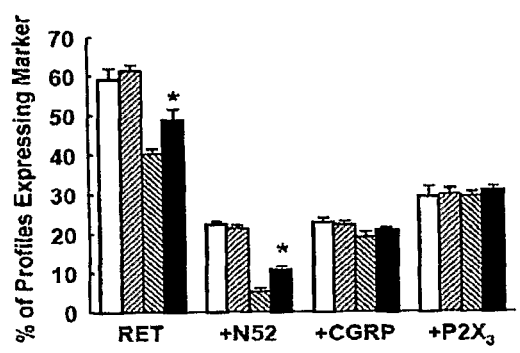

Differential Expression of GFRα3 in Peripheral Nerves Correlates with Recovery of Sensory Modalities Since neublastin acts through the GFRα3 receptor coupled to the RET signaling protein, DRC-induced changes in expression of GFRα3 or RET among the different types of peripheral nerves may influence their regeneration. Neublastin treatment did not alter GFRα3 or RET expression in any fiber types of sham-operated animals. When measured 14 days after sham surgery, the percentage of DRG profiles that expressed GFRα3 were 34±1.9 and 33±3.1 for the vehicle-treated and neublastin-treated groups, respectively and the percentage expressing RET were 59±2.8 and 61±1.5 (FIG. 7A). The percent of profiles from the DRG of rats with DRC and vehicle treatment that expressed GFRα3 was significantly increased to 52±1.8 whereas that expressing RET was decreased to 40±1.23 (FIG. 7B). Treatment with neublastin largely normalized these changes, and the corresponding percentages of DRG profiles expressing GFRα3 was 47±6.14 and that expressing or RET was 49±2.72. Co-labeling for GFRα3 or for RET and for either N52, CGRP or P2X3 was examined in order to identify changes in myelinated peripheral nerves (N52) and unmyelinated peptidergic (CGRP) and non-peptidergic ($P2X_3$) nociceptors. 14±0.5% of the DRG profiles of sham-operated, vehicle-treated rats co-labeled GFRα3 and N52 and 22±0.85% of the DRG profiles co-expressed RET and N52, indicating that a significant proportion of myelinated peripheral nerves are subject to modulation by neublastin. Neublastin treatment did not change these proportions in sham-operated rats (FIGS. 7A and 7B). The proportion of DRG profiles that labeled both GFRα3 and N52 was reduced to 5±1.2% and that expressing N52 and RET was reduced to 5±0.9% (FIGS. 7A and 7B). In contrast, there was a near doubling of DRG profiles immunoreactive for either CGRP or $P2X_3$ and for GFRα3 while those also labeling RET remained unchanged (FIGS. 7A and 7B). Neublastin treatment resulted in a normalization of the proportions of DRG neuronal populations expressing these markers (FIGS. 7A and 7B), and largely prevented the loss of co-labeling for N52 and either GFαc3 or RET caused by DRC.

Example 8

Neublastin does not Alter the Characteristics of the DREZ

Immunoreactivity to glial fibrillary acidic protein (GFAP), which identifies astrocytes, and to ED1, which labels activated microglia, were markedly increased by DRC. Treatment with neublastin did not produce any changes in labeling for either GFAP or ED1 after DRC injury. Therefore, it is likely that the regeneration of axons and functional recovery of sensory modalities induced by neublastin was due to enhanced survival of the axon growth cones and stimulation of regeneration rather than to a breakdown of the inhibitory barriers in the DREZ.

Example 9

Timing-Based Neublastin Administration Post Dorsal Root Injury Facilitates Functional Recovery Clinically, immediate treatment to a dorsal root injury is not always available. To mimic clinical conditions and to examine the window of opportunity for neublastin treating dorsal root injury efficiently, neublastin was administrated in a delayed time courses.

When given subcutaneously starting at day 2 post dorsal root injury, neublastin restored the thermal and mechanical function almost completely, reached the maximum recovery at day 10 post injury, and then remained at a similar level until the end of experiment at day 28 post root injury. When injected subcutaneously starting at day 4 post dorsal rhizotomy, neublastin recovered thermal function fully and recovered mechanical function partially. Neublastin treatment still significantly restored the mechanical response at day 9 post surgery after 3 injections, compared to the vehicle treatment. When given at day 7 post root injury, neublastin exerted the ability of restoring the function to the thermal stimuli significantly, but lost the ability of responding to mechanical stimuli.

In line with the shifts of functional recovery in delayed neublastin treatment, the labeling of three types of afferents in spinal dorsal horn also changed with the time of delayed neublastin treatment. The dramatic changes were seen in CTB labeling, though CGRP and P2X3 labeling also exhibited some changes. When neublastin was given starting at day 2 post root injury, the spinal density of CTB labeling was around 50% of normal level at day 28 post dorsal root injury. When neublastin was given at day 4 post root injury, the number was about 25%, when neublastin was injected starting at day 7 post dorsal root crush, the number was about 5 percent. However, the CGRP and P2X3 labeling was maintained 35% or above of the normal level at day 28 post root injury for delayed neublastin treatments. Delayed vehicle treatment did not change the labeling density of the three types of sensory axons in the spinal dorsal horn.

Example 10

Systemic Neublastin Promotes Peripheral Nerve Regeneration and Recovery of Mechanical and Thermal Hypersensitivity in Animals that have Undergone Nerve Crush Distal to the Dorsal Root Ganglia The L5 spinal nerve of anesthetized rats was exposed and (i) tightly ligated with sutures according to the procedure of Kim and Chung (Kim et al. (1992) *Pain* 50:355-63) ("nerve ligation"), (ii) crushed as described in Example 1 ("nerve crush"), or (iii) cut ("nerve section"). Sham surgery was processed under the same procedures without nerve injury. Rat neublastin or saline vehicle was given subcutaneously on a Monday, Wednesday, and Friday schedule immediately after surgery for a total of 6 injections over 2 weeks.

The Von Frey (Chaplan et al. (1994) J. Neurosci. Meth. 53:55-63) and Hargreaves (Hargreaves et al. (1988) Pain 32:77-88) behavioral tests were used to monitor tactile and thermal pain responses, respectively. Five weeks post-surgery, the neuronal tracers CTB and Dextran were injected into the sciatic nerve at the mid-thigh (distal to the nerve injury). Six weeks post-surgery, rats were perfused for histological study.

Figure 8A:
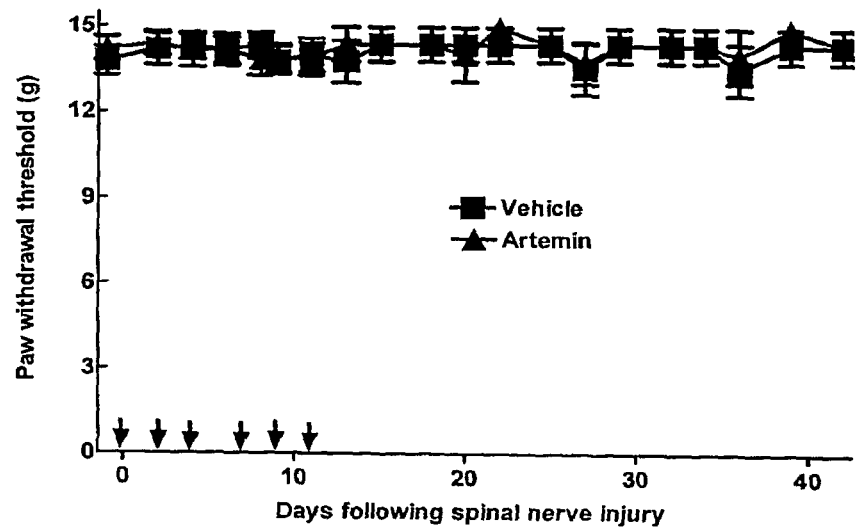
FIGS. 8A-8D are graphs depicting the effect of systemic neublastin (artemin) administration on tactile pain responses following sham L5 spinal nerve surgery (FIG. 8A), L5 spinal nerve section (FIG. 8B), L5 spinal nerve ligation (FIG. 8C), and L5 spinal nerve crush (FIG. 8D). Arrows indicate the time when each injection of neublastin or vehicle was made.
Figure 8B:
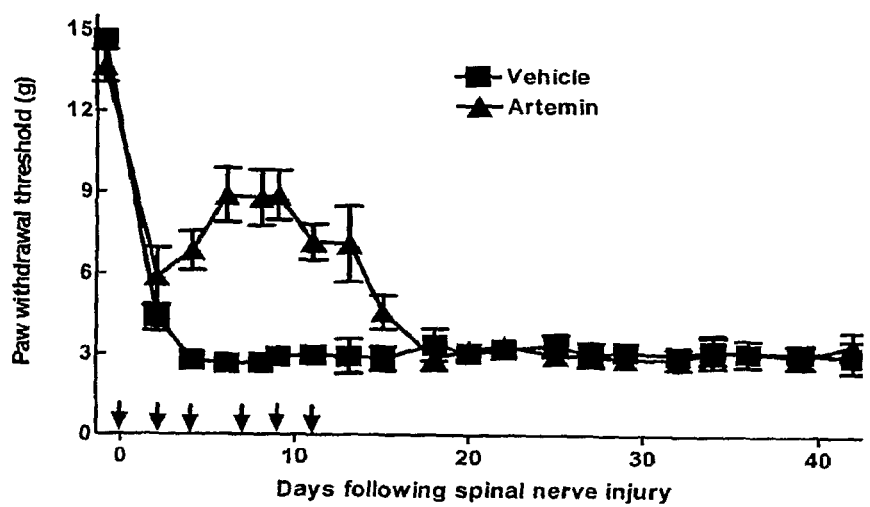
Figure 8C:
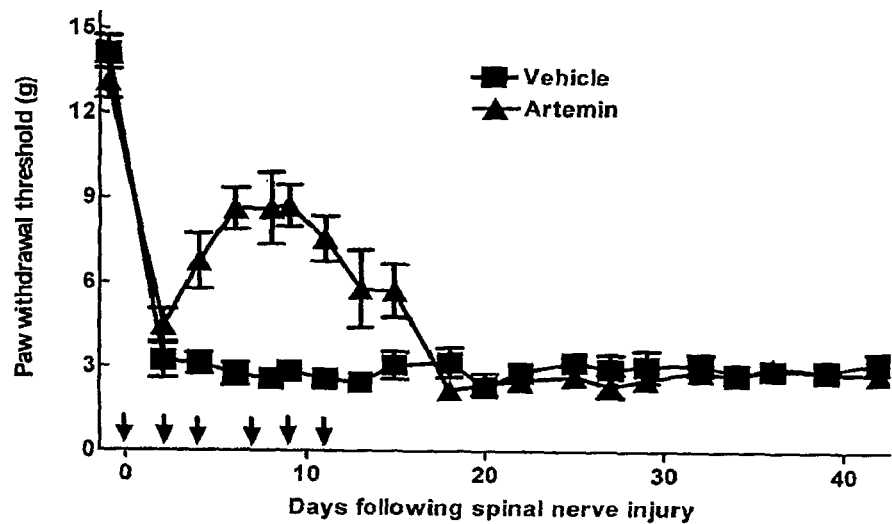
Figure 8D:
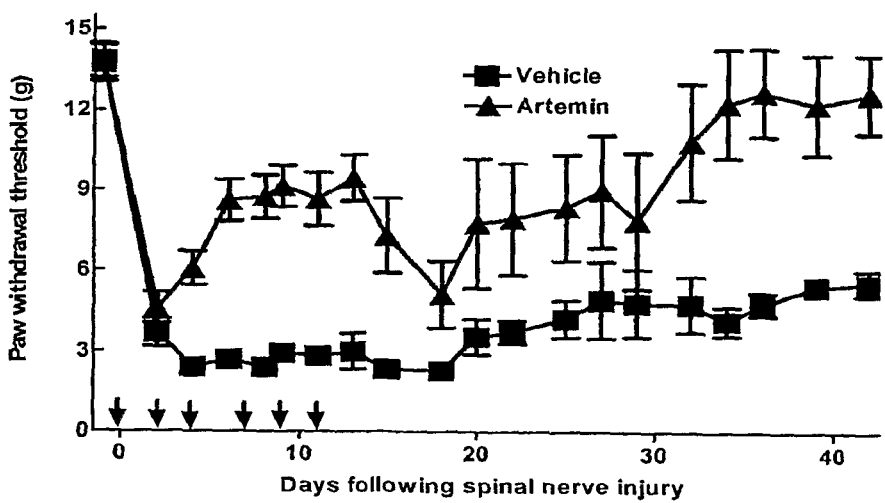
Figure 9A:
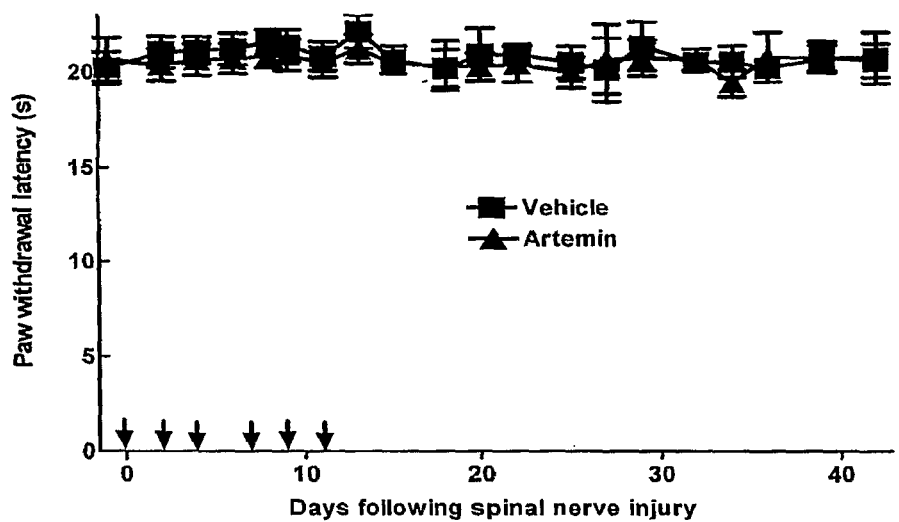
FIGS. 9A-9D are graphs depicting the effect of systemic neublastin (artemin) administration on thermal pain responses following sham L5 spinal nerve surgery (FIG. 9A), L5 spinal nerve section (FIG. 9B), L5 spinal nerve ligation (FIG. 9C), and L5 spinal nerve crush (FIG. 9D). Arrows indicate the time when each injection of neublastin or vehicle was made.
Figure 9B:
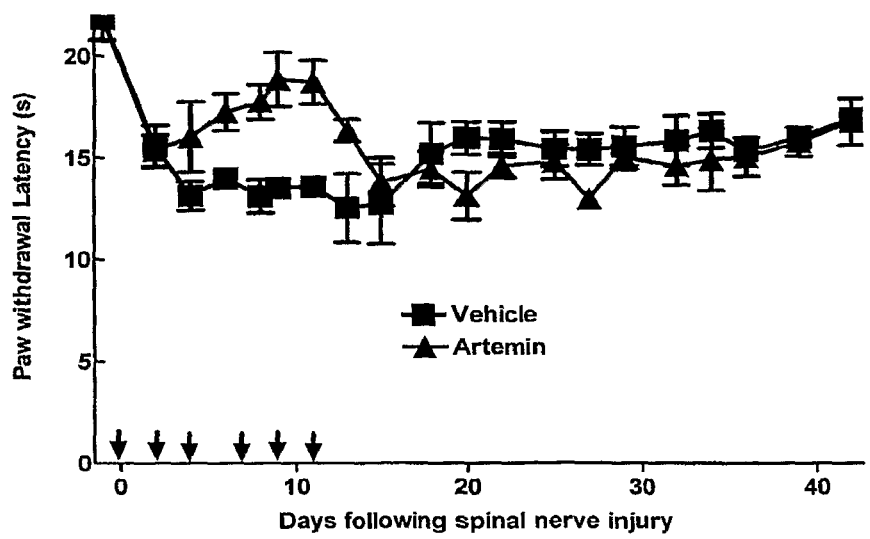
Figure 9C:
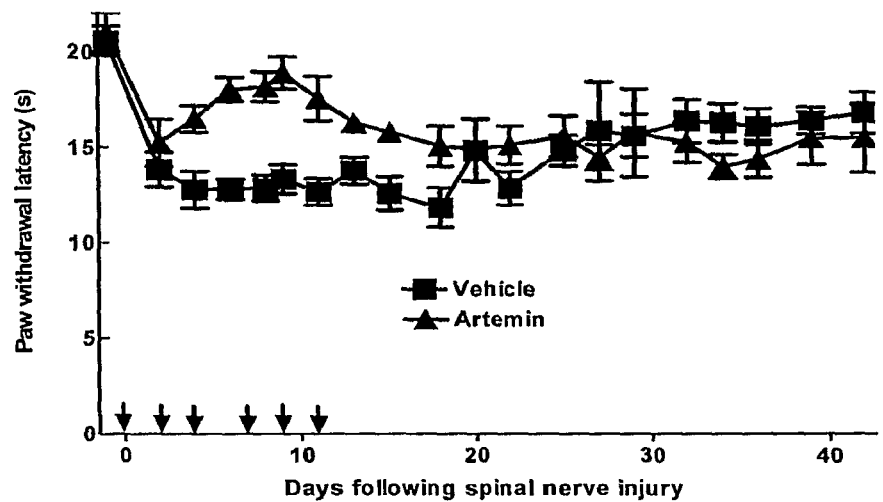
Figure 9D:
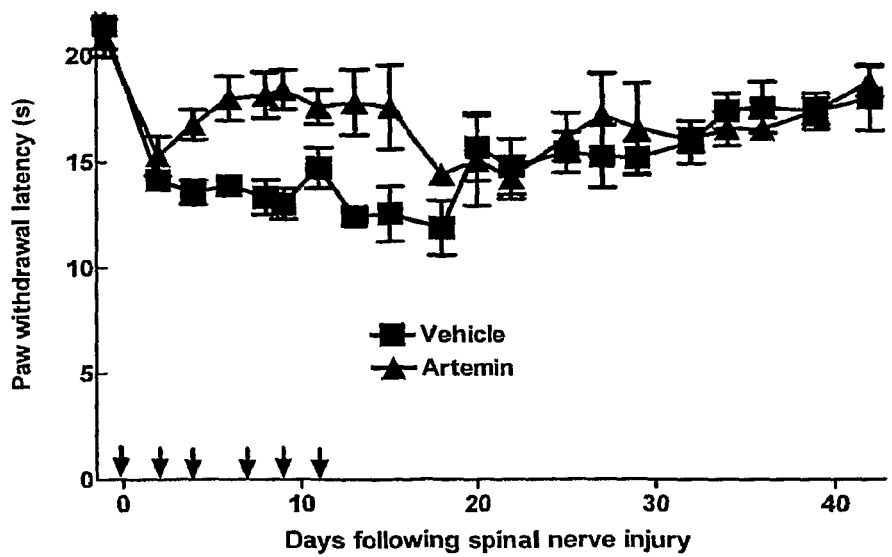

Tactile allodynia and thermal hyperalgesia measurements were recorded on injured and sham injured animals treated with neublastin or vehicle. Animals with nerve injury and treated with vehicle showed no improvement in pain responses, with little change in responses throughout the six week evaluation (FIGS. 8A-8D and 9A-9D). Acute systemic neublastin administration caused an improvement of both tactile allodynia (FIGS. 8A-8D) and thermal hyperalgesia (FIGS. 9A-9D) thresholds following nerve section, nerve ligation, and nerve crush. In the nerve crush rats, the recovery of tactile allodynia persisted after the neublastin administration was terminated and was observed throughout the entire six week evaluation period (FIG. 8D).

Dextran, a neuronal tracer for labeling small diameter sensory fibers in the normal peripheral nervous system, was injected into the sciatic nerve (mid-thigh, distal to the nerve injury) and labeled neurons in the L5 DRG were subsequently examined. Systemic neublastin administration was found to promote regeneration of Dextran-labeled sensory fibers in the L5 nerve crush rats.

CTB, a neuronal tracer for labeling myelinated sensory fibers in the normal peripheral nervous system, was injected into the sciatic nerve (mid-thigh, distal to the nerve injury) and labeled neurons in the L5 DRG were subsequently examined. Systemic neublastin administration was found to promote regeneration of CTB-labeled sensory fibers in the L5 nerve crush rats.

IB4, CGRP, and N52 immunolabelling was employed to visualize, respectively, non-peptidergic sensory fibers, peptidergic sensory fibers, and myelinated sensory fibers (these three biomarkers collectively label all populations of sensory biomarkers). Systemic neublastin administration was found to promote regeneration of all three types of sensory fibers in the L5 spinal nerve (distal to the crush site).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of regenerating sensory nerve fibers, the method comprising administering to a human subject that has suffered an impairment or loss of sensory function and damage to or loss of sensory nerve fibers, an amount of a polypeptide effective to regenerate the sensory nerve fibers, the method resulting in the regeneration of the sensory nerve fibers and a persistent restoration of sensory function in the subject,
the polypeptide consisting of amino acids 15-113 of SEQ ID NO:1, amino acids 15-113 of SEQ ID NO:2, amino acids 15-113 of SEQ ID NO:3, amino acids 15-113 of SEQ ID NO: 4, amino acids 15-113 of SEQ ID NO:8, or amino acids 15-113 of SEQ ID NO: 9,
wherein the polypeptide, when dimerized, binds to a complex containing GFRα3 and RET, and
wherein the polypeptide is administered to the subject within one month following the damage to or loss of nerve fibers.

2. The method of claim 1, wherein the nerve fibers are large nerve fibers.

3. The method of claim 1, wherein the nerve fibers are small nerve fibers.

4. The method of claim 1, wherein the subject has suffered damage to, or loss of, dorsal root nerve fibers.

5. The method of claim 1, wherein the subject has suffered damage to or loss of nerve fibers distal to the dorsal root ganglia.

6. The method of claim 1, wherein the nerve fibers are nerve fibers of the skin and the administration of the polypeptide results in skin reinnervation.

7. The method of claim 1, wherein the polypeptide is administered to the subject within 48 hours following the damage to or loss of nerve fibers.

8. The method of claim 1, wherein the polypeptide is administered to the subject within seven days following the damage to or loss of nerve fibers.

9. The method of claim 1 wherein the polypeptide is administered to the subject in two or more doses following the damage to or loss of nerve fibers.

10. The method of claim 1, wherein administration of the polypeptide to the subject is terminated within six months following the damage to or loss of nerve fibers.

11. . The method of claim 1, wherein administration of the polypeptide to the subject is terminated within one month following the damage to or loss of nerve fibers.

12. The method of claim 1 wherein administration of the polypeptide to the subject is terminated within two weeks following the damage to or loss of nerve fibers.

13. The method of claim 1, wherein the damage to or loss of nerve fibers is a result of a nerve crush injury.

14. The method of claim 1, wherein the polypeptide is administered to the subject via systemic administration.

15. The method of claim 1, wherein the polypeptide is administered to the subject via subcutaneous administration.

16. The Method of claim 1, wherein the polypeptide is administered to the subject via intravenous administration.

17. The method of claim 1, wherein the polypeptide is administered locally to damaged neural tissue.

18. The method of claim 1, wherein the polypeptide consists of amino acids 15-113 of SEQ ID NO:2, amino acids 15-113 of SEQ ID NO:3, amino acids 15-113 of SEQ ID NO:4, amino acids 15-113 of SEQ ID NO: 8 or amino acids 15-113 of SEQ ID NO: 9.

19. The method of claim 1, wherein the polypeptide consists of amino acids 15-113 of SEQ ID NO:1.

* * * * *

SEQUENCE LISTING

<160> NUMBER OF SEQ ID NOS: 12

<210> SEQ ID NO 1
<211> LENGTH: 113
<212> TYPE: PRT
<213> ORGANISM: Homo sapiens

<400> SEQUENCE: 1

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 2
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 2

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Arg Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 3
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 3

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Glu Ala Arg Ser Pro His Asp Leu Ser Leu Ala Ser Leu Leu Gly Ala

```
                    50                  55                  60
Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                     85                  90                  95

Thr Trp Arg Thr Val Asp Arg Leu Ser Ala Thr Ala Cys Gly Cys Leu
                100                 105                 110

Gly

<210> SEQ ID NO 4
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 4

Ala Gly Gly Pro Gly Ser Arg Ala Arg Ala Gly Ala Arg Gly Cys
 1               5                  10                  15

Arg Leu Arg Ser Gln Leu Val Pro Val Arg Ala Leu Gly Leu Gly His
                 20                  25                  30

Arg Ser Asp Glu Leu Val Arg Phe Arg Phe Cys Ser Gly Ser Cys Arg
             35                  40                  45

Arg Ala Glu Ser Pro His Asp Leu Ser Leu Ala Ser Leu Leu Gly Ala
 50                  55                  60

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                     85                  90                  95

Thr Trp Arg Thr Val Asp Arg Leu Ser Ala Thr Ala Cys Gly Cys Leu
                100                 105                 110

Gly

<210> SEQ ID NO 5
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 5

Ala Gly Gly Pro Gly Ser Arg Ala Arg Ala Gly Ala Arg Gly Cys
 1               5                  10                  15

Arg Leu Arg Ser Gln Leu Val Pro Val Arg Ala Leu Gly Leu Gly His
                 20                  25                  30

Arg Ser Asp Glu Leu Val Arg Phe Arg Phe Cys Ser Gly Ser Cys Glu
             35                  40                  45

Glu Ala Arg Ser Pro His Asp Leu Ser Leu Ala Ser Leu Leu Gly Ala
 50                  55                  60

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                     85                  90                  95

Thr Trp Arg Thr Val Asp Arg Leu Ser Ala Thr Ala Cys Gly Cys Leu
                100                 105                 110

Gly
```

<210> SEQ ID NO 6
<211> LENGTH: 99
<212> TYPE: PRT
<213> ORGANISM: Artificial Sequence
<220> FEATURE:
<223> OTHER INFORMATION: Synthetically generated peptide

<400> SEQUENCE: 6

Gly Cys Arg Leu Arg Ser Gln Leu Val Pro Val Arg Ala Leu Gly Leu
1               5                   10                  15

Gly His Arg Ser Asp Glu Leu Val Arg Phe Arg Phe Cys Ser Gly Ser
            20                  25                  30

Cys Glu Glu Ala Arg Ser Pro His Asp Leu Ser Leu Ala Ser Leu Leu
        35                  40                  45

Gly Ala Gly Ala Leu Arg Pro Pro Gly Ser Arg Pro Val Ser Gln
    50                  55                  60

Pro Cys Cys Arg Pro Thr Arg Tyr Glu Ala Val Ser Phe Met Asp Val
65                  70                  75                  80

Asn Ser Thr Trp Arg Thr Val Asp Arg Leu Ser Ala Thr Ala Cys Gly
                85                  90                  95

Cys Leu Gly

<210> SEQ ID NO 7
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 7

Ala Ala Gly Ala Arg Gly Cys Arg Leu Arg Ser Gln Leu Val Pro Val
1               5                   10                  15

Arg Ala Leu Gly Leu Gly His Arg Ser Asp Glu Leu Val Arg Phe Arg
            20                  25                  30

Phe Cys Ser Gly Ser Cys Glu Glu Ala Arg Ser Pro His Asp Leu Ser
        35                  40                  45

Leu Ala Ser Leu Leu Gly Ala Gly Ala Leu Arg Pro Pro Gly Ser
    50                  55                  60

Arg Pro Val Ser Gln Pro Cys Cys Arg Pro Thr Arg Tyr Glu Ala Val
65                  70                  75                  80

Ser Phe Met Asp Val Asn Ser Thr Trp Arg Thr Val Asp Arg Leu Ser
                85                  90                  95

Ala Thr Ala Cys Gly Cys Leu Gly
            100

<210> SEQ ID NO 8
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 8

Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

```
Glu Ala Glu Ser Pro His Asp Leu Ser Leu Ala Ser Leu Leu Gly Ala
        50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 9
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 9

Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
                20                  25                  30

Arg Ser Asp Glu Leu Val Arg Phe Arg Phe Cys Ser Gly Ser Cys Glu
            35                  40                  45

Arg Ala Glu Ser Pro His Asp Leu Ser Leu Ala Ser Leu Leu Gly Ala
        50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 10
<211> LENGTH: 220
<212> TYPE: PRT
<213> ORGANISM: Homo sapiens

<400> SEQUENCE: 10

Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
                20                  25                  30

Leu Ser Ser Val Ala Glu Ala Ser Leu Gly Ser Ala Pro Arg Ser Pro
            35                  40                  45

Ala Pro Arg Glu Gly Pro Pro Val Leu Ala Ser Pro Ala Gly His
        50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
            100                 105                 110

Ser Arg Ala Arg Ala Ala Gly Ala Arg Gly Cys Arg Leu Arg Ser Gln
        115                 120                 125
```

-continued

Leu Val Pro Val Arg Ala Leu Gly Leu Gly His Arg Ser Asp Glu Leu
        130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
    210                 215                 220

<210> SEQ ID NO 11
<211> LENGTH: 224
<212> TYPE: PRT
<213> ORGANISM: Mus musculus

<400> SEQUENCE: 11

Met Glu Leu Gly Leu Ala Glu Pro Thr Ala Leu Ser His Cys Leu Arg
1               5                   10                  15

Pro Arg Trp Gln Ser Ala Trp Trp Pro Thr Leu Ala Val Leu Ala Leu
                20                  25                  30

Leu Ser Cys Val Thr Glu Ala Ser Leu Asp Pro Met Ser Arg Ser Pro
            35                  40                  45

Ala Ala Arg Asp Gly Pro Ser Pro Val Leu Ala Pro Pro Thr Asp His
        50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Ala
                85                  90                  95

Leu Gln Ser Pro Pro Ala Ala Leu Arg Gly Ala Arg Ala Ala Arg Ala
            100                 105                 110

Gly Thr Arg Ser Ser Arg Ala Arg Thr Thr Asp Ala Arg Gly Cys Arg
        115                 120                 125

Leu Arg Ser Gln Leu Val Pro Val Ser Ala Leu Gly Leu Gly His Ser
130                 135                 140

Ser Asp Glu Leu Ile Arg Phe Arg Phe Cys Ser Gly Ser Cys Arg Arg
145                 150                 155                 160

Ala Arg Ser Gln His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
        195                 200                 205

Trp Arg Thr Val Asp His Leu Ser Ala Thr Ala Cys Gly Cys Leu Gly
    210                 215                 220

<210> SEQ ID NO 12
<211> LENGTH: 224
<212> TYPE: PRT
<213> ORGANISM: Rattus norvegicus

<400> SEQUENCE: 12

Met Glu Leu Gly Leu Gly Glu Pro Thr Ala Leu Ser His Cys Leu Arg
1               5                   10                  15

-continued

```
Pro Arg Trp Gln Pro Ala Leu Trp Pro Thr Leu Ala Ala Leu Ala Leu
            20                  25                  30

Leu Ser Ser Val Thr Glu Ala Ser Leu Asp Pro Met Ser Arg Ser Pro
            35                  40                  45

Ala Ser Arg Asp Val Pro Ser Pro Val Leu Ala Pro Pro Thr Asp Tyr
 50                  55                  60

Leu Pro Gly Gly His Thr Ala His Leu Cys Ser Glu Arg Thr Leu Arg
 65                  70                  75                  80

Pro Pro Pro Gln Ser Pro Gln Pro Ala Pro Pro Pro Pro Gly Pro Ala
                85                  90                  95

Leu Gln Ser Pro Pro Ala Ala Leu Arg Gly Ala Arg Ala Ala Arg Ala
            100                 105                 110

Gly Thr Arg Ser Ser Arg Ala Arg Ala Thr Asp Ala Arg Gly Cys Arg
            115                 120                 125

Leu Arg Ser Gln Leu Val Pro Val Ser Ala Leu Gly Leu Gly His Ser
    130                 135                 140

Ser Asp Glu Leu Ile Arg Phe Arg Phe Cys Ser Gly Ser Cys Arg Arg
145                 150                 155                 160

Ala Arg Ser Pro His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
            195                 200                 205

Trp Arg Thr Val Asp His Leu Ser Ala Thr Ala Cys Gly Cys Leu Gly
    210                 215                 220
```